(12) United States Patent
Mahfouz

(10) Patent No.: US 9,937,046 B2
(45) Date of Patent: Apr. 10, 2018

(54) METHOD OF GENERATING A PATIENT-SPECIFIC BONE SHELL

(71) Applicant: ZIMMER, INC., Warsaw, IN (US)

(72) Inventor: Mohamed Rashwan Mahfouz, Knoxville, TN (US)

(73) Assignee: ZIMMER, INC., Warsaw, IN (US)

( * ) Notice: Subject to any disclaimer, the term of this patent is extended or adjusted under 35 U.S.C. 154(b) by 704 days.

(21) Appl. No.: 14/505,916

(22) Filed: Oct. 3, 2014

(65) Prior Publication Data
US 2015/0120031 A1 Apr. 30, 2015

Related U.S. Application Data

(63) Continuation of application No. 13/203,010, filed as application No. PCT/US2010/025467 on Feb. 25, 2010, now Pat. No. 8,884,618.
(Continued)

(51) Int. Cl.
*G06K 9/00* (2006.01)
*A61F 2/30* (2006.01)
(Continued)

(52) U.S. Cl.
CPC ........ *A61F 2/30942* (2013.01); *A61B 8/4245* (2013.01); *A61B 34/10* (2016.02);
(Continued)

(58) Field of Classification Search
CPC ... A61B 17/68; A61B 17/8066; A61B 17/866; A61B 2034/2051; A61B 2090/367;
(Continued)

(56) References Cited

U.S. PATENT DOCUMENTS 6,701,174 B1 * 3/2004 Krause ................ A61B 17/025
378/21
7,239,908 B1 7/2007 Alexander et al.
(Continued)

FOREIGN PATENT DOCUMENTS

JP 3049021 A 11/1998
JP 3049021 B2 3/2000
(Continued)

OTHER PUBLICATIONS

Sun Y et al : "Discussions of Knee Joint Segmentation", Biomedical and Pharmaceutical Engineering, 2006. ICBPE 2006. International Conference On, IEEE, PI, Jan. 1, 2006 (Jan. 1, 2006).
(Continued)

*Primary Examiner* — Aklilu Woldemariam
(74) *Attorney, Agent, or Firm* — Norton Rose Fulbright Canada LLP

(57) ABSTRACT

The exemplary embodiments of the present disclosure are described and illustrated below to encompass methods and devices for designing patient specific prosthetic cutting jigs and, more specifically, to devices and methods for segmenting bone of the knee and the resulting cutting guides themselves. Moreover, the present disclosure relates to systems and methods for manufacturing customized surgical devices, more specifically, the present disclosure relates to automated systems and methods of arthroplasty cutting guides, systems and methods for image segmentation in generating computer models of knee joint.

11 Claims, 43 Drawing Sheets

Related U.S. Application Data

(60) Provisional application No. 61/222,560, filed on Jul. 2, 2009, provisional application No. 61/208,509, filed on Feb. 25, 2009.

(51) Int. Cl.

| | | |
|---|---|---|
| *A61F 2/38* | (2006.01) | |
| *G06F 17/18* | (2006.01) | |
| *G06F 19/00* | (2018.01) | |
| *A61B 8/00* | (2006.01) | |
| *G06T 19/00* | (2011.01) | |
| *A61F 2/36* | (2006.01) | |
| *A61F 2/40* | (2006.01) | |
| *A61B 34/10* | (2016.01) | |

(52) U.S. Cl.
CPC .......... *A61F 2/3094* (2013.01); *A61F 2/3601* (2013.01); *A61F 2/389* (2013.01); *A61F 2/3859* (2013.01); *A61F 2/4003* (2013.01); *G06F 17/18* (2013.01); *G06F 19/3437* (2013.01); *G06T 19/00* (2013.01); *A61B 2034/102* (2016.02); *A61B 2034/108* (2016.02); *A61F 2/38* (2013.01); *A61F 2002/30943* (2013.01); *A61F 2002/30948* (2013.01); *A61F 2002/3863* (2013.01); *A61F 2002/3895* (2013.01); *G06K 9/00* (2013.01); *G06T 2210/41* (2013.01)

(58) Field of Classification Search
CPC ......... A61B 34/20; A61B 5/103; A61B 34/10; A61B 5/1121; A61B 5/4514; A61B 2034/102; A61B 2034/108; A61B 8/4245; A61B 5/4504; A61B 5/4528; A61F 2002/30948; A61F 2002/30952; A61F 2002/30943; A61F 2002/3863; A61F 2002/3895; A61F 2/3094; A61F 2/30942; A61F 2/3601; A61F 2/38; A61F 2/3859; A61F 2/389; A61F 2002/30957; A61F 2250/0058; B33Y 50/00; G05B 19/4099; G06F 17/18; G06F 19/3437; G06T 19/00; G06T 2210/04; G06T 7/0014
USPC .............. 382/128, 131, 132, 151, 154, 203; 600/409, 426, 443, 300, 411, 425, 416, 600/637, 439
See application file for complete search history.

(56) References Cited

U.S. PATENT DOCUMENTS

| | | | |
|---|---|---|---|
| 7,269,241 B2 | 9/2007 | Siltanen et al. | |
| 7,340,082 B2 | 3/2008 | Janssen et al. | |
| 7,724,931 B2 | 5/2010 | Kuth et al. | |
| 8,050,473 B2 | 11/2011 | Udupa et al. | |
| 8,062,302 B2* | 11/2011 | Lang | A61B 5/4528 606/84 |
| 8,150,132 B2 | 4/2012 | Nakamura | |
| 8,219,177 B2* | 7/2012 | Smith | A61B 5/06 600/411 |
| 8,545,569 B2* | 10/2013 | Fitz | A61F 2/30756 623/14.12 |
| 8,644,568 B1* | 2/2014 | Hoffmann | G06T 19/20 382/128 |
| 8,945,230 B2* | 2/2015 | Lang | A61F 2/30942 623/20.31 |
| 2002/0055692 A1 | 5/2002 | Tanaka et al. | |
| 2003/0040806 A1 | 2/2003 | MacDonald | |
| 2003/0181831 A1 | 9/2003 | Tanaka et al. | |
| 2004/0039259 A1 | 2/2004 | Krause et al. | |
| 2004/0068187 A1 | 4/2004 | Krause et al. | |
| 2004/0098132 A1 | 5/2004 | Andriacchi et al. | |
| 2005/0010444 A1 | 1/2005 | Iliff | |
| 2005/0197814 A1 | 9/2005 | Aram et al. | |
| 2006/0195198 A1 | 8/2006 | James | |
| 2007/0081706 A1 | 4/2007 | Zhou et al. | |
| 2007/0118243 A1 | 5/2007 | Schroeder et al. | |
| 2007/0168225 A1 | 7/2007 | Haider et al. | |
| 2007/0179626 A1 | 8/2007 | de la Barrera et al. | |
| 2007/0226986 A1 | 10/2007 | Park et al. | |
| 2007/0249967 A1* | 10/2007 | Buly | A61B 5/1121 600/595 |
| 2007/0255288 A1 | 11/2007 | Mahfouz et al. | |
| 2007/0276214 A1 | 11/2007 | Dachille et al. | |
| 2008/0031412 A1* | 2/2008 | Lang | G01B 15/045 378/54 |
| 2008/0058945 A1 | 3/2008 | Hajaj et al. | |
| 2008/0097187 A1 | 4/2008 | Gielen et al. | |
| 2008/0262624 A1 | 10/2008 | White et al. | |
| 2009/0043556 A1 | 2/2009 | Axelson et al. | |
| 2010/0023015 A1* | 1/2010 | Park | A61B 17/15 606/87 |
| 2010/0305708 A1* | 12/2010 | Lang | A61F 2/30942 623/20.18 |
| 2011/0304332 A1* | 12/2011 | Mahfouz | A61F 2/3094 324/309 |
| 2011/0305379 A1* | 12/2011 | Mahfouz | A61F 2/3094 382/131 |
| 2012/0089235 A1* | 4/2012 | Conway | A61B 17/8066 623/22.24 |

FOREIGN PATENT DOCUMENTS

| | | |
|---|---|---|
| JP | 2004202126 | 7/2004 |
| JP | 2006263241 | 10/2006 |
| WO | 00/35346 A2 | 6/2000 |
| WO | 01/078015 A2 | 4/2001 |
| WO | 01/078015 A2 | 10/2001 |
| WO | 2004/049981 A | 11/2003 |
| WO | 2004049981 | 6/2004 |
| WO | 2008112996 A1 | 9/2008 |

OTHER PUBLICATIONS

Jurgen Fripp et al: "Automatic Segmentation of Articular Cartilage in Magnetic Resonance Images of the Knee", Oct. 29, 2007 (Oct. 29, 2007), Medical Image Computing and Computer-Assisted Intervention—MICCAI 2007; ( Lecture Notes in Computer Science), Springer Berlin Heidelberg, Berlin, Heidelberg, pp. 186-194.

Shapiro et al., "Similarity-Based Retrieval for Biomedical Applications", Studies in Computational Intelligence, Springer, 73, pp. 355-387, 2008.

Dennis et al, Coventry Award Paper, Multicenter Determination of In Vivo Kinematics After Total Knee Arthroplasty, Clinical Orthopaedics and Related Research, No. 416, pp. 37-57, c 2003 Lippincott Williams & Wilkins, Inc., USA.

Mahfouz, et al, A Robust Method for Registration of Three-Dimensional Knee Implant Models to Two-Dimensional Fluoroscopy Images, IEEE Transactions on Medical Imaging, vol. 22, No. 12, Dec. 2003, c 2003 IEEE, USA.

Mahfouz et al, Automatic methods for characterization of sexual dimorphism of adult femora: distal femur, Computer Methods in Biomechanics and Biomedical Engineering, 2007, iFirst article, 1-10, c 2007 Taylor & Francis, GB.

Mahfouz et al, Patella sex determination by 3D statistical shape models and nonlinear classifiers, Forensic Science International, FSI-5154, pp. 1-10, c 2007 Elsevier Ireland Ltd., IE.

Merkl et al, Unsupervised Three-Dimensional Segmentation of Medical Images Using an Anatomical Bone Atlas, published in biomedical conference in Singapore, Dec. 2005, University of Tennessee/Department of Mechanical, Aerospace and Biomedical Engrg., Knoxville, TN, USA.

International Search Report and Written Opinion dated Jan. 5, 2009 for PCT/US08/09837.

(56) References Cited

OTHER PUBLICATIONS

International Preliminary Report on Patentability Opinion dated Apr. 1, 2010 for PCT/US08/09837.
International Search Report and Written Opinion dated Jul. 1, 2010 for PCT/US2010/025466.
International Preliminary Report on Patentability dated Jun. 7, 2011 for PCT/US2010/025466.
International Search Report and Written Opinion dated Apr. 23, 2010 for PCT/US2010/025467.
International Preliminary Report on Patentability dated Oct. 11, 2011 for PCT/US2010/025467.

* cited by examiner

Physician

| Column Name | Condensed Type |
|---|---|
| 🔑 Physician_ID | uniqueidentifier |
| Physician_Type | text |
| Physician_Hospital | text |
| Physician_Last_Name | text |
| Physician_First_Name | text |
| Physician_Middle_Initial | text |
| Physician_Address1 | text |
| Physician_Address2 | text |
| Physician_City | text |
| Physician_State | text |
| Physician_Country | text |
| Physician_Zip | text |
| Physician_Phone | text |
| Physician_Notes | text |

RegisterCase

| Column Name | Condensed Type |
|---|---|
| 🔑 Case_ID | uniqueidentifier |
| Physician_ID | uniqueidentifier |
| Case_Title | text |
| Case_Last_Name | text |
| Case_First_Name | text |
| Case_Middle_Initial | text |
| Case_Status | text |
| Date_of_Study | text |
| Date_of_Surgery | text |
| Case_Height | text |
| Case_Weight | text |
| Case_Notes | text |
| Case_Type | char(50) |

PersonalCase

| Column Name | Condensed Type |
|---|---|
| 🔑 Case_ID | uniqueidentifier |
| Case_SSN | text |
| Case_Address1 | text |
| Case_Address2 | text |
| Case_City | text |
| Case_State | text |
| Case_Country | text |
| Case_Zip | text |
| Case_Gender | text |
| Case_Date_of_Birth | text |
| Case_Home_Phone | text |
| Case_Work_Phone | text |
| rowguid | uniqueidentifier |
| Case_Ethnicity | text |

VolumeData

| Column Name | Condensed Type |
|---|---|
| 🔑 Volume_ID | uniqueidentifier |
| Image_Modality | char(50) |
| Volume_Path | text |

TwoDImages

| Column Name | Condensed Type |
|---|---|
| 🔑 Volume_ID | uniqueidentifier |
| Image_Modality | char(50) |
| Image | image |
| Bone_ID | uniqueidentifier |

Femur

| Column Name | Condensed Type |
|---|---|
| 🔑 Femur_ID | uniqueidentifier |
| Volume_ID | uniqueidentifier |
| Image_ID | char(50) |
| Condition | text |
| Deformity_Type | text |
| Preview_Image | image |
| Orientation | char(10) |
| Leg_ID | uniqueidentifier |
| Foot_Print | text |
| Three_D_Contour | text |
| Femur_Landmarks | text |
| Femur_Axes | text |

Patella

| Column Name | Condensed Type |
|---|---|
| 🔑 Patella_ID | uniqueidentifier |
| Volume_ID | uniqueidentifier |
| Image_ID | char(50) |
| Condition | text |
| Deformity_Type | text |
| Preview_Image | image |
| Orientation | char(10) |
| Leg_ID | uniqueidentifier |
| Three_D_Contour | text |
| Patella_Landmarks | char(10) |
| Patella_Axes | char(10) |

Tibia

| Column Name | Condensed Type |
|---|---|
| 🔑 Tibia_ID | uniqueidentifier |
| Volume_ID | uniqueidentifier |
| Image_ID | char(50) |
| Condition | text |
| Deformity_Type | text |
| Preview_Image | image |
| Orientation | char(10) |
| Leg_ID | uniqueidentifier |
| Foot_Print | text |
| Three_D_Contour | text |
| Tibia_Landmarks | text |
| Tibia_Axes | text |

FIG. 4A

Implant

| Column Name | Condensed Type |
|---|---|
| Implant_ID | uniqueidentifier |
| Implant_Type | text |
| Implant_Material | text |
| Manufacturer_ID | uniqueidentifier |
| Implant_Footprint | text |
| Implant_Size | text |
| Implant_Family | char(200) |
| Implant_Size | char(10) |
| Implant_Model | text |
| Implant_Name | text |
| Implant_Clipping_Planes | text |

ImplantFitting

| Column Name | Condensed Type |
|---|---|
| Implant_ID | uniqueidentifier |
| Bone_ID | uniqueidentifier |
| Fit_ID | uniqueidentifier |

Manufacturer

| Column Name | Condensed Type |
|---|---|
| Manufacturer_ID | uniqueidentifier |
| Manufacturer_Name | char(200) |
| Manufacturer_Address | text |
| Manufacturer_Zip | char(10) |
| Manufacturer_Telephone | char(20) |
| Manufacturer_Fax | char(10) |
| Manufacturer_web | text |

FIG. 4B

METHOD OF GENERATING A PATIENT-SPECIFIC BONE SHELL

CROSS REFERENCE TO RELATED APPLICATIONS

The present application is a continuation of U.S. Non-Provisional patent application Ser. No. 13/203,010 which claims the benefit of U.S. Provisional Patent Application Ser. No. 61/208,509, filed Feb. 25, 2009 and entitled, DEFORMABLE ARTICULATING TEMPLATE, and U.S. Provisional Patent Application Ser. No. 61/222,560, filed Jul. 2, 2009 and entitled, CUSTOMIZED ORTHOPAEDIC IMPLANTS AND RELATED METHODS, the disclosure of each of which is hereby incorporated by reference.

FIELD OF THE INVENTION

The present disclosure relates to systems and methods for manufacturing customized surgical devices, more specifically, the present disclosure relates to automated systems and methods of arthroplasty cutting guides, systems and methods for image segmentation in generating computer models of knee joint.

INTRODUCTION TO THE INVENTION

The success of TKA operations depends on the restoration of correct knee alignment. It has been demonstrated that the key to the stability of the knee joint is the restoration of the mechanical axis with balanced flexion and extension gaps. Traditionally, intramedullary and extramedullary jigs were used to assist in orientation of the femoral and tibial components. Computer assisted surgery has been developed to assist surgeons in proper positioning and orientation of the components. However, surgical navigation systems are not widely used in hospitals. Main arguments against surgical navigation systems are the high costs and extra time spent in the operating room, in addition to a steep learning curve.

The desire for a simple and accurate system as a substitute motivated the orthopaedic industry to develop a technique involving the use of patient specific cutting jigs. Magnetic resonance images (MRIs) of the patient's hip, knee, and ankle anatomy are used to generate a model of specific patient anatomy. From these images, software is used to create virtual 3D models of the femur and tibia and orient these bones in space. Implant size is determined with the software and virtual bone resections are mapped to perform implant positioning and alignment using disposable custom guides that fit on the patient's bone to determine pin placement for the standard resection instrumentation of the implant manufacturer.

However, a number of drawbacks are associated with MRI including scanning cost, increased scanning time, geometrical distortion, and the need to standardize the scanning protocol among different MRI vendors. Recently Computerized Tomography CT is being used as well but the radiation associated with the procedure may not be favorable for some patients. An alternative approach to MRI or CT is to use the statistical anatomical shape analysis methodology to model the hylene cartilage accurately using x-rays and/or ultrasound.

Statistical anatomical shape analysis has rapidly established itself as an invaluable tool in the design process for orthopaedic implants and patient specific solutions. Thus, the intelligent Cartilage System (iCS) was conceived, with the goal of putting statistical anatomical shape analysis to accurately model cartilage thickness and contours to produce custom cutting guides (or Jigs). The guides are designed to place the cuts such that the knee is returned to its normal anatomical state before the degeneration of cartilage. The iCS system is built on the foundational merger of statistics and three-dimensional bone modeling.

The iCS platform represents a cohesive software system encompassing multidimensional medical imaging, computer aided design (CAD) and computer graphics features integrated for designing patient specific cutting jigs. The promise of coordinated interaction, efficiency, and mass customization allows iCS to address the complexities of increased patients' volume with accuracy and speed. A smart database composed of bone and cartilage atlases provide technology utilized within the customized module for custom jig generation. By reducing turn-around time in the current custom jig process, the iCS platform minimizes the risk of bottlenecks.

The database stores patient information following HIPPA regulations. Data from different imaging modalities will be attached with each patient including DICOM from MRI/CT, X-ray images, and ultrasound. Reconstructed bones and cartilage are stored in the database. Virtual templating data including calculated landmarks, axes, implant sizing, and placement information are also stored in the database. This component implements both relational and XML schema to provide a powerful tool for data storage and manipulation.

Bone Cartilage Reconstruction Subsystem: This module involves reconstruction of both bones and soft tissues either by segmentation from MRI, CT, PET or Ultrasound or direct reconstruction from RF signals as in microwave imaging and US or three dimensional bone reconstruction from 2D X-ray images, flow chart outlining this subsystem can be found in FIG. 4.

Segmentation of medical imaging can be roughly divided into two categories; Structural and Statistical. Structural approaches are based on spatial properties of the image pixels such as edges and regions. Statistical approaches rely on the probability distribution of intensity values in labeling the image regions. Image intensities and their corresponding class labels are considered to be random variables. Therefore, the statistical approaches tend to solve the problem of evaluating the class label, given the image intensity value. Previous segmentation attempts have combined one or more of these methods trying to overcome the limitations of individual methods.

Most of the segmentation using the edge oriented approach is semi-auto segmentation, where it is used to extract contours, optimizing contour and propagating it to neighbor slices. Image preprocessing and gradient operators can be used to enhance typical region growing methods. If an organ is known to be present in a certain area of an image by placement of a seed (either manually or automatically), the region can expand until it reaches the contrast boundaries of the organ. Parameters can vary to change the momentum of the growing, making the algorithm more or less sensitive to small changes in grayscale.

Region-Oriented Segmentation with Knowledge-Based Labeling is a pixel classification technique based on the homogeneity of some features of the object. Various approaches such as knowledge based with uncertainty reasoning, static domain knowledge from high order features extraction, fuzzy logic, long term and short term memory modeling, as well as unsupervised clustering have been used in this area. They yield very good result with MRI images because of the high contrast between soft tissues. The global interpretation error of the brain is 3.1% and the interpretations error for sub-regions of the brain is 9%.

The watershed approach has been used in combination with various other segmentation methods in hopes of improving accuracy. The watershed algorithm is simply explained with a 3D plot of the grayscale intensities in an image; the "water" fills the valleys of the image until two valleys meet. This provides connectivity information about different areas of the image by relying on grayscale values. Pre-processing with edge enhancement such as Sobel filters and texture analysis can aid in detection of different organs.

Clustering algorithms are non-supervised algorithms that iterate between segmenting the image and characterizing the properties of each class until well defined image clusters are formed. Examples for such algorithms are the K-means algorithm, the fuzzy c-means algorithm, the expectation maximization (EM) algorithm and Self-Organized Neural Networks. The K-means clustering algorithm clusters data by iteratively computing a mean intensity for each class and segmenting the image by classifying each pixel in the class with the closest mean. It was used to segment the brain. The number of classes was assumed to be three, representing cerebrospinal fluid, gray matter, and white matter.

The fuzzy c-means algorithm generalizes the K-means algorithm, allowing for soft segmentations based on fuzzy set theory. The EM algorithm applies the same clustering principles with the assumption that the data follows Gaussian mixture model. It iterates between computing the posterior probabilities and computing maximum likelihood estimates of the means, covariances, and mixing coefficients of the model. Since algorithms do not directly incorporate spatial modeling they are sensitive to noise and intensity inhomogeneities. This can be overcome by using Markov Random Field modeling.

Morphological Operators like binary morphology has been used in several segmentation systems, the basic idea in morphology is to convolve an image with a given mask (known as the structuring element), and to binarize the result of the convolution using a given function. Examples are: Erosion, Dilation, Opening and Closing.

Statistical approaches like thresholding label regions of the image by using its intensity value histogram. A maximum and minimum threshold defines the region on interest depending on the knowledge base. For example, in CT, rough segmentation of organs can be achieved by thresholding the image according to the Hounsfield unit ranges for organs of interest. It has been applied in digital mammography, in which two classes of tissue are typically present; healthy and tumorous. Limitations of depending solely on such a method are due to the usual overlap of organ intensities' intervals, intensity inhomogeneities, and sensitivity to noise and image artifacts. Since thresholding does not take into account the spatial characteristics of the image, any artifact that distorts the image histogram can eventually affect the segmentation results. Nevertheless, thresholding remains to be an initial step in many segmentation algorithms Variations on classical thresholding have been proposed for medical image segmentation that incorporate information based on local intensities and connectivity.

Deformable template matching is performed with 2D deformable contours, which involves detection of the contour, tracking, matching and optimizing the error of the match. In segmentation, 2D deformable contour is applied with an atlas, which permits mapping between the image data and the atlas by constrained minimization of predefined data. A 3D deformable surface is also realized by tracking contour changes between slides. Bayesian statistics is commonly used for determining the model priors or likelihood in order to separate the organ of interest with its neighboring organs. In general, the approach produces good results for small and local shape changes. It is also suitable for large and global misalignments or deformations. A major improvement came from using principle geodesic analysis, which determines the mean shape of an object and the principle mode of variation, and an m-rep model, which the object is represented as a set of connected meshes of medial atoms. This method yields excellent results for automatic segmentation of kidneys with 0.12 cm mean surface separation and 88.8% volume overlay as compare to manual segmentation.

Knowledge-Based Approach with Blackboard Architecture system, in general, is an area of shared memory that contains a problem to be solved and a number of different processes. The blackboard is continually constructed and updated along the reasoning process. The labeling of the anatomical structures of the image data is done by matching the structure in the image to the corresponding objects in the models. The data from the image and the model are transformed into a common, parametric feature space for comparisons. The low and high level features extracted are written to the blackboard and compare with the model. The result is also written onto the blackboard to guide further matching. Long-term memory on the descriptions and relationships of the object can be written into the knowledge base.

Four Dimensional Markov Random Fields (MRF), present a method using a 4D probabilistic atlases to segment moving targets such as the heart. The atlases predict the time and space variance based on a priori information; the algorithm also incorporates spatial and temporal contextual information using 4D Markov Random Fields (MRF). Global connectivity filters finish the segmentation, using the largest connected structure as a starting point. The results presented were very favorable for segmentation of the heart and are not limited to MRI images. The results for left ventricle (LV) 96%, myocardium 92% and right ventricle (RV) 92% as compared to manually segmented models.

Our system utilizes the information from any three dimensional imaging modality to extract gradients information combined with statistical atlases to extract bone boundaries, and cartilage interfaces. Bellow detailed description of each these bone reconstruction modalities.

BRIEF DESCRIPTION OF THE DRAWINGS

FIG. 4A and FIG. 4B are an exemplary listing of database table details for the database shown in FIG. 1.

DETAILED DESCRIPTION OF EXEMPLARY EMBODIMENTS

The exemplary embodiments of the present disclosure are described and illustrated below to encompass methods and devices for designing patient specific prosthetic cutting jigs and, more specifically, to devices and methods for segmenting bone of the knee and the resulting cutting guides themselves. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
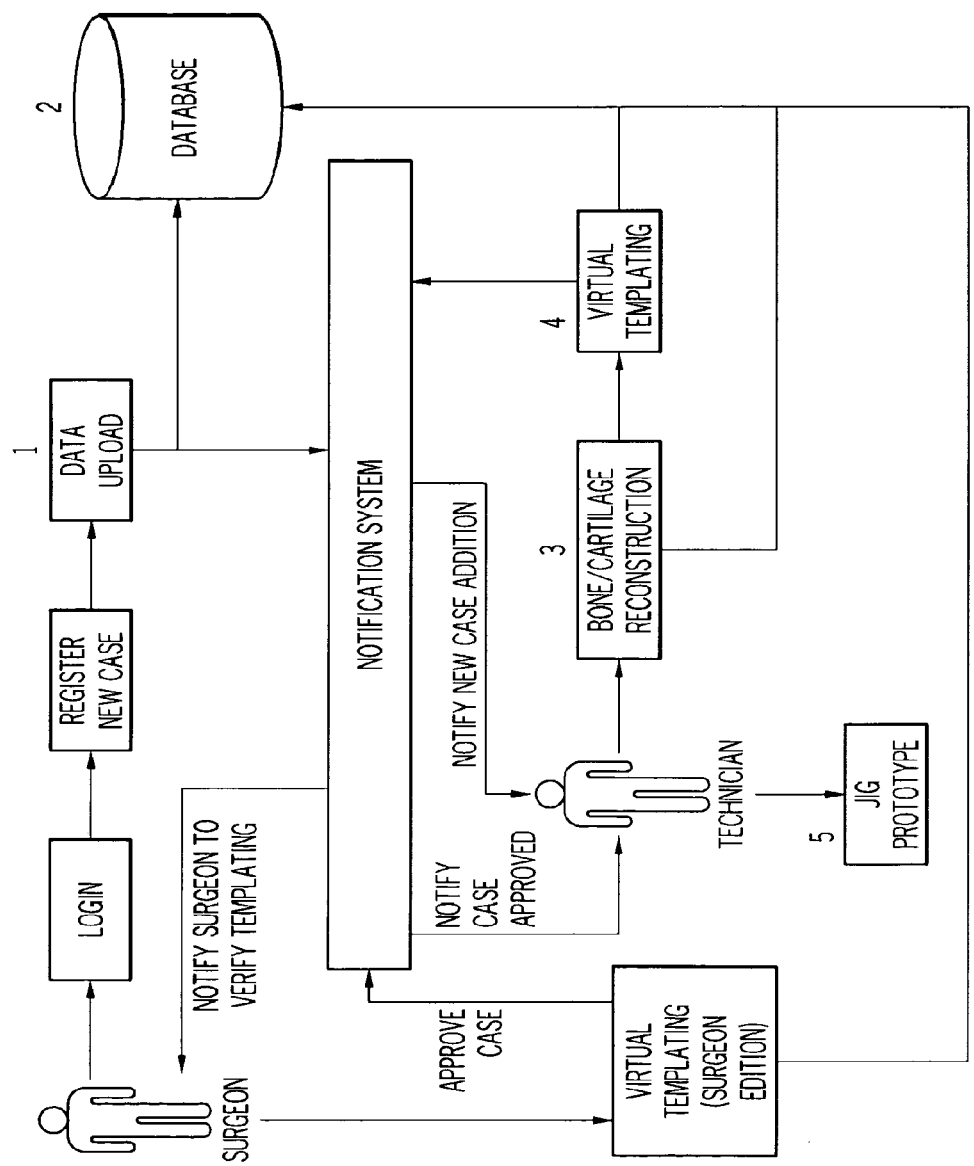
FIG. 1 is a diagram of an exemplary iCS system overview.
Figure 2:
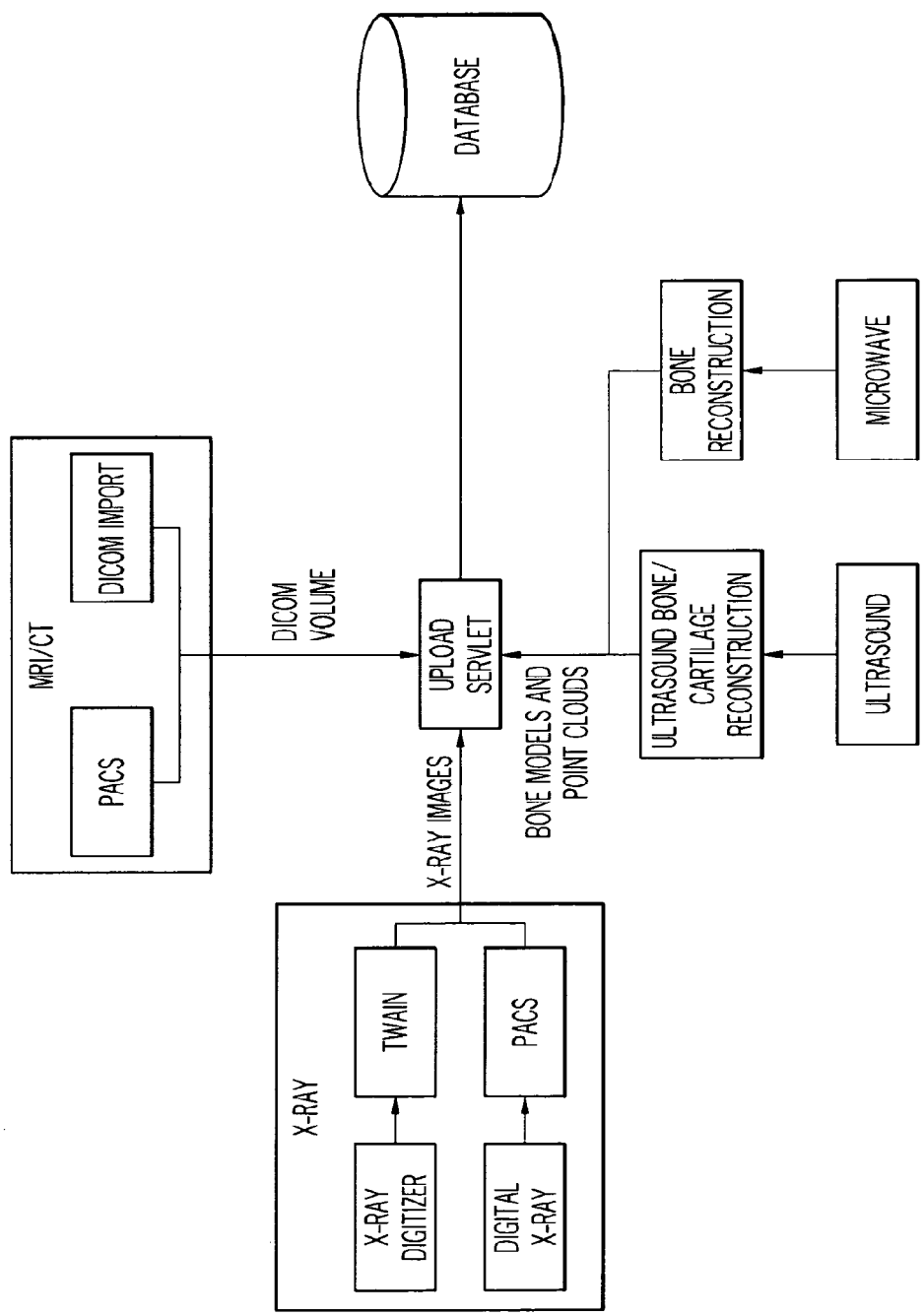
FIG. 2 is a diagram of an exemplary data upload subsystem as shown in FIG. 1.
Figure 3:
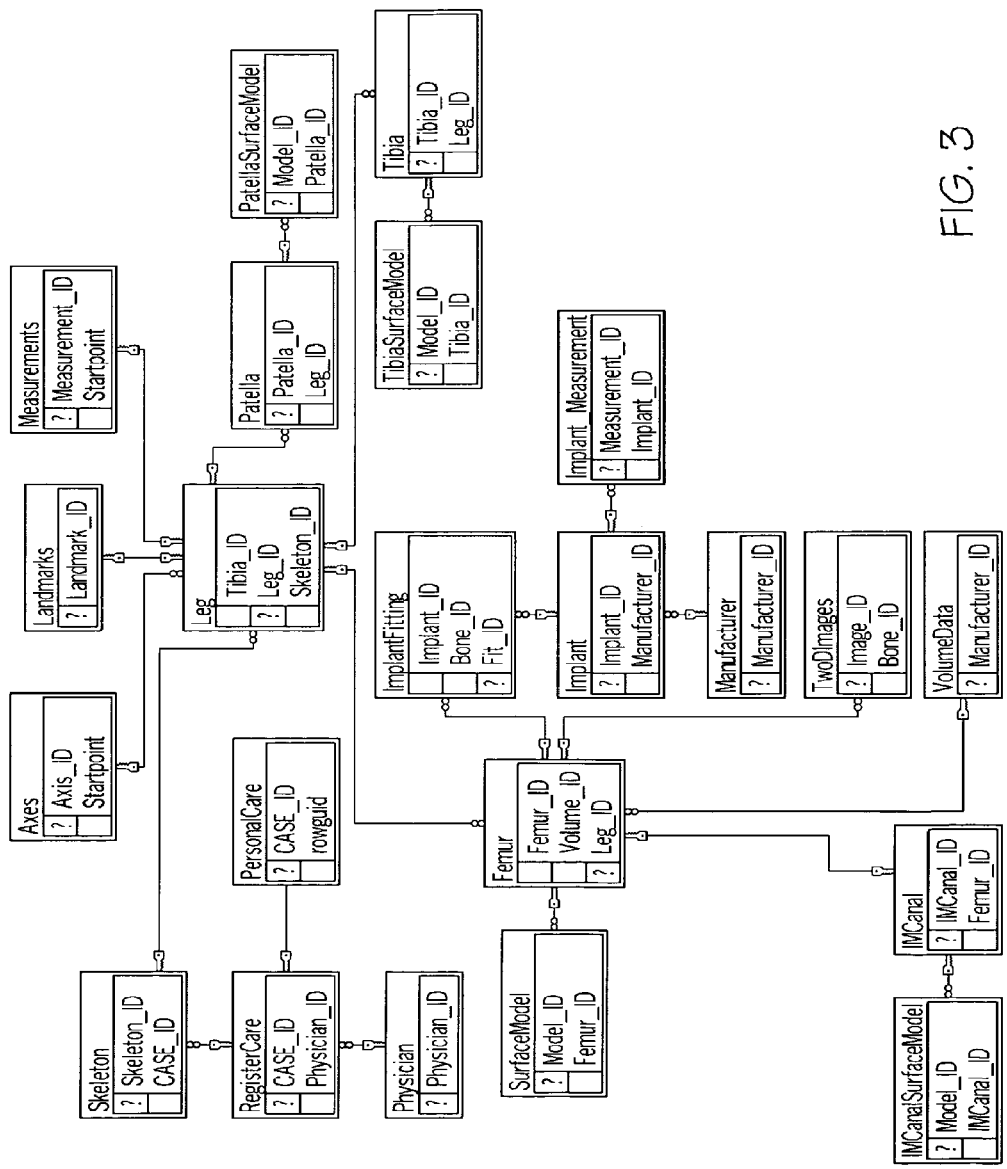
FIG. 3 is an exemplary database schema as shown in FIG. 1.
Figure 5:
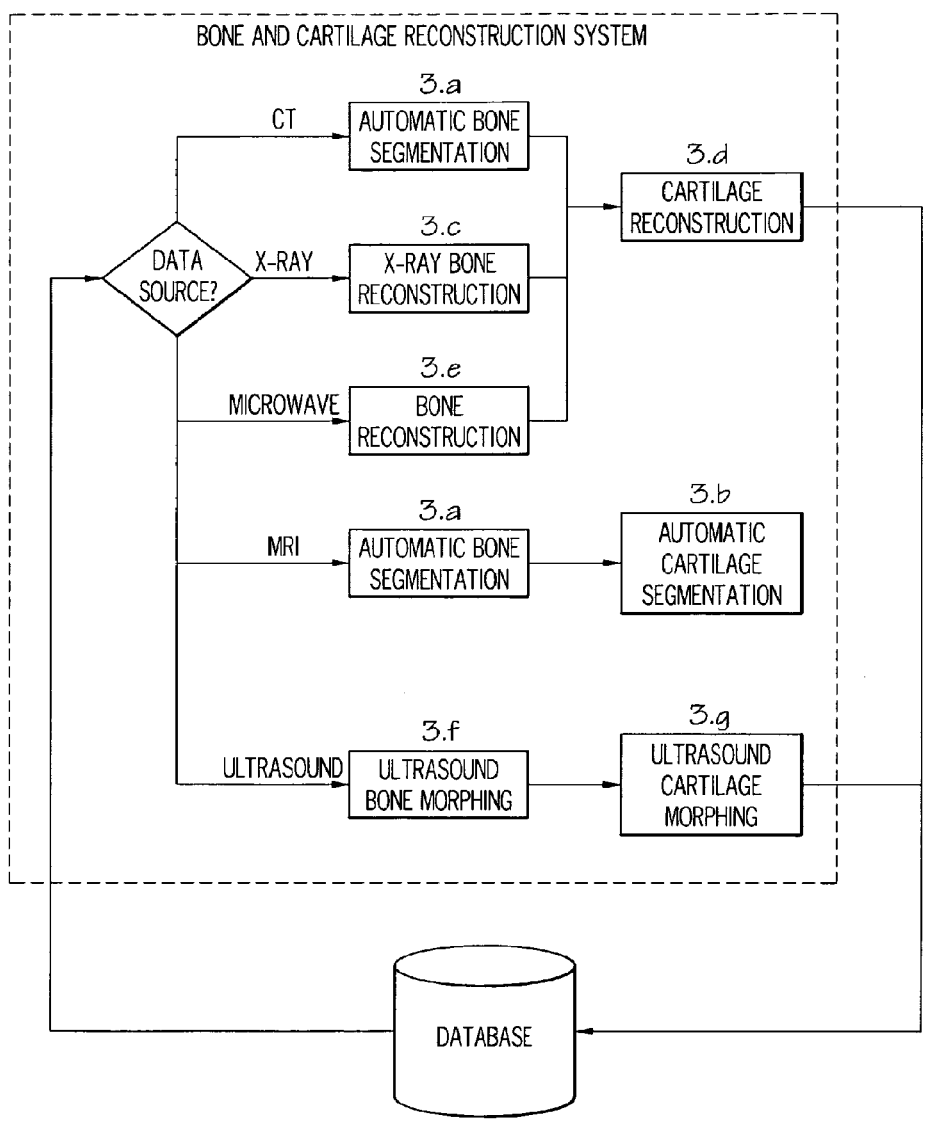
FIG. 5 is an exemplary schematic diagram of a bone/cartilage reconstruction subsystem as shown in FIG. 1.
Figure 6:
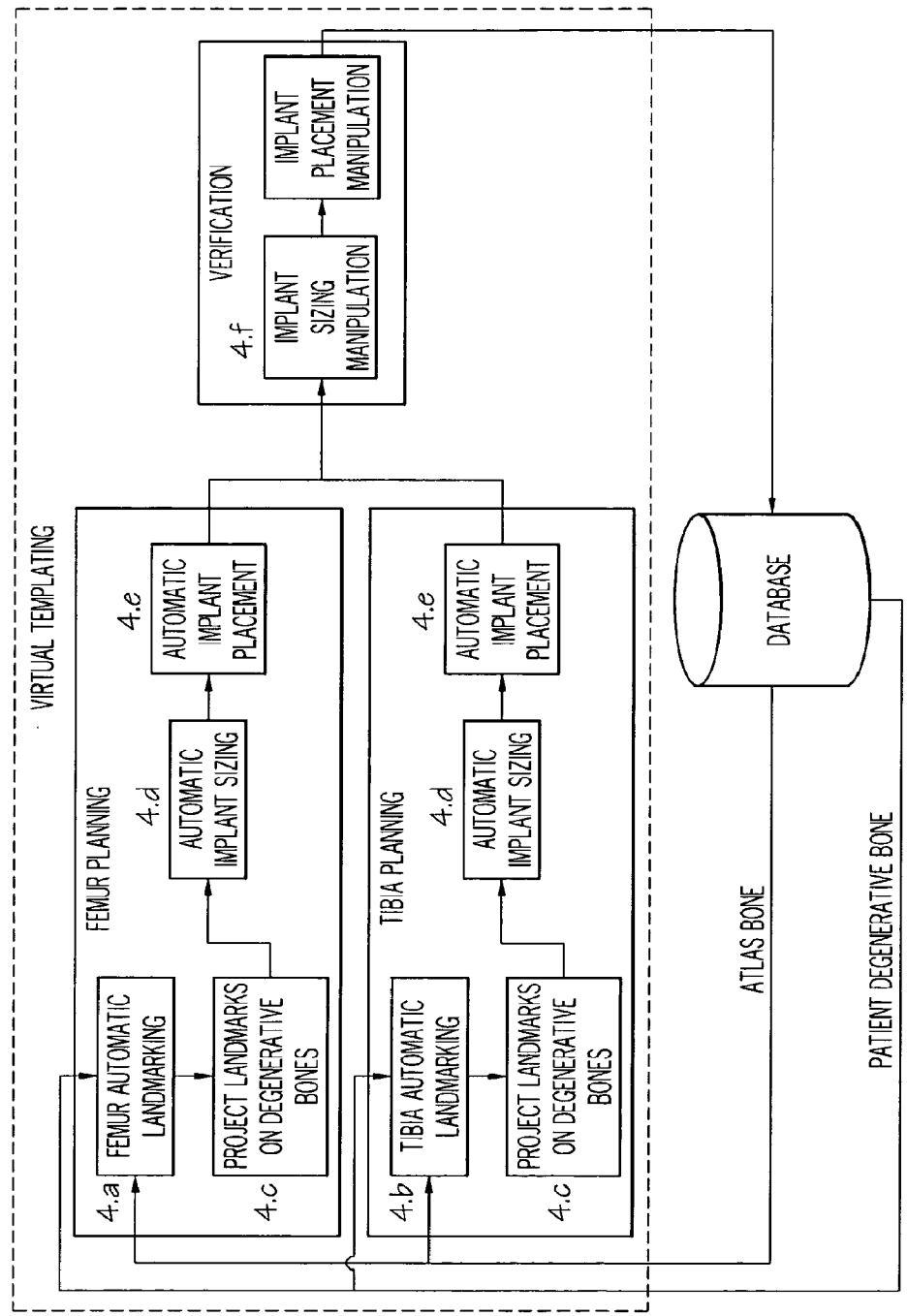
FIG. 6 is an exemplary diagram of a virtual templating subsystem as shown in FIG. 1.
Figure 7:
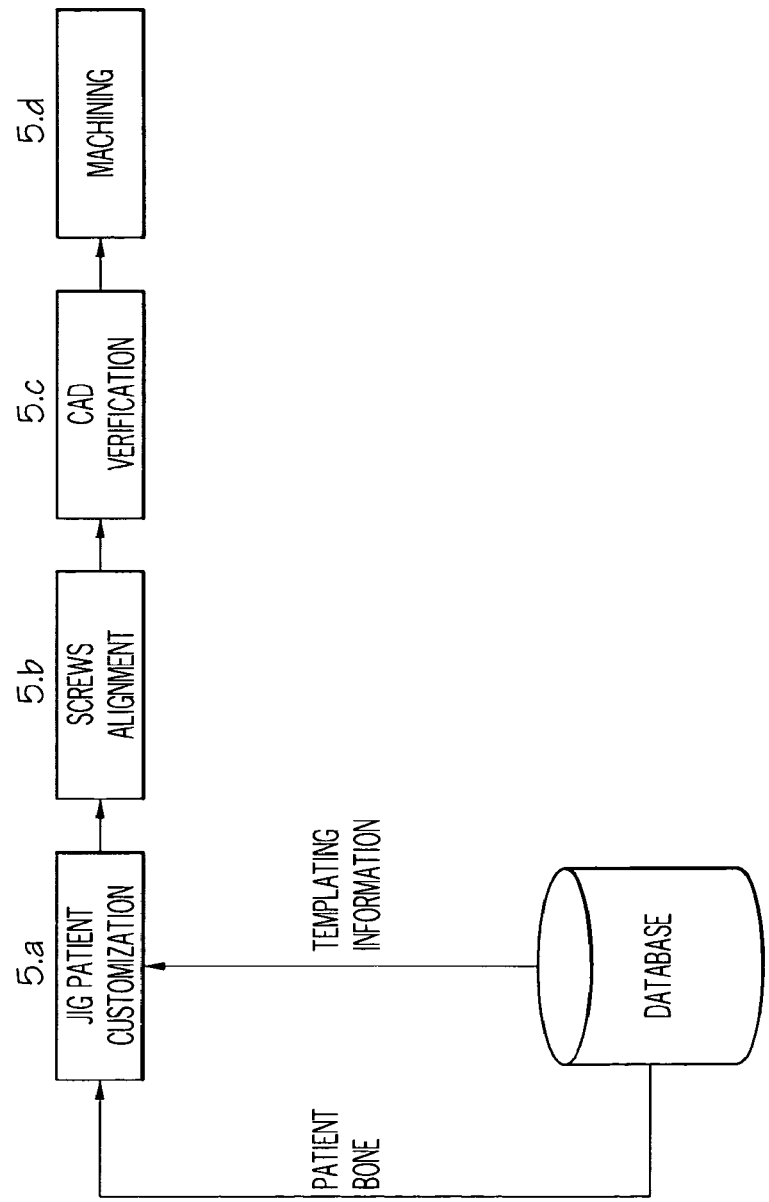
FIG. 7 is an exemplary diagram of a jig prototyping subsystem as shown in FIG. 1.

Referring to FIG. 1, an outline of an exemplary overall system includes a surgeon creating a new case and requesting a custom jig and uploading the patient imaging data, this is followed by system notifying company engineers about the new case. Next step involves creating patient specific bone and cartilage which are then used to find implant the best fit the patient, upon completion of preoperative planning surgeon is notified to review and approve the planning. Once surgeon approves the planning a custom cutting jig is automatically created for patient that translates the preoperative planning into the operating room.

FIGS. 2-7 outline the main components of the system this includes a data upload component, database component, bone cartilage reconstruction component, virtual templating and jig generation component.

Figure 8:
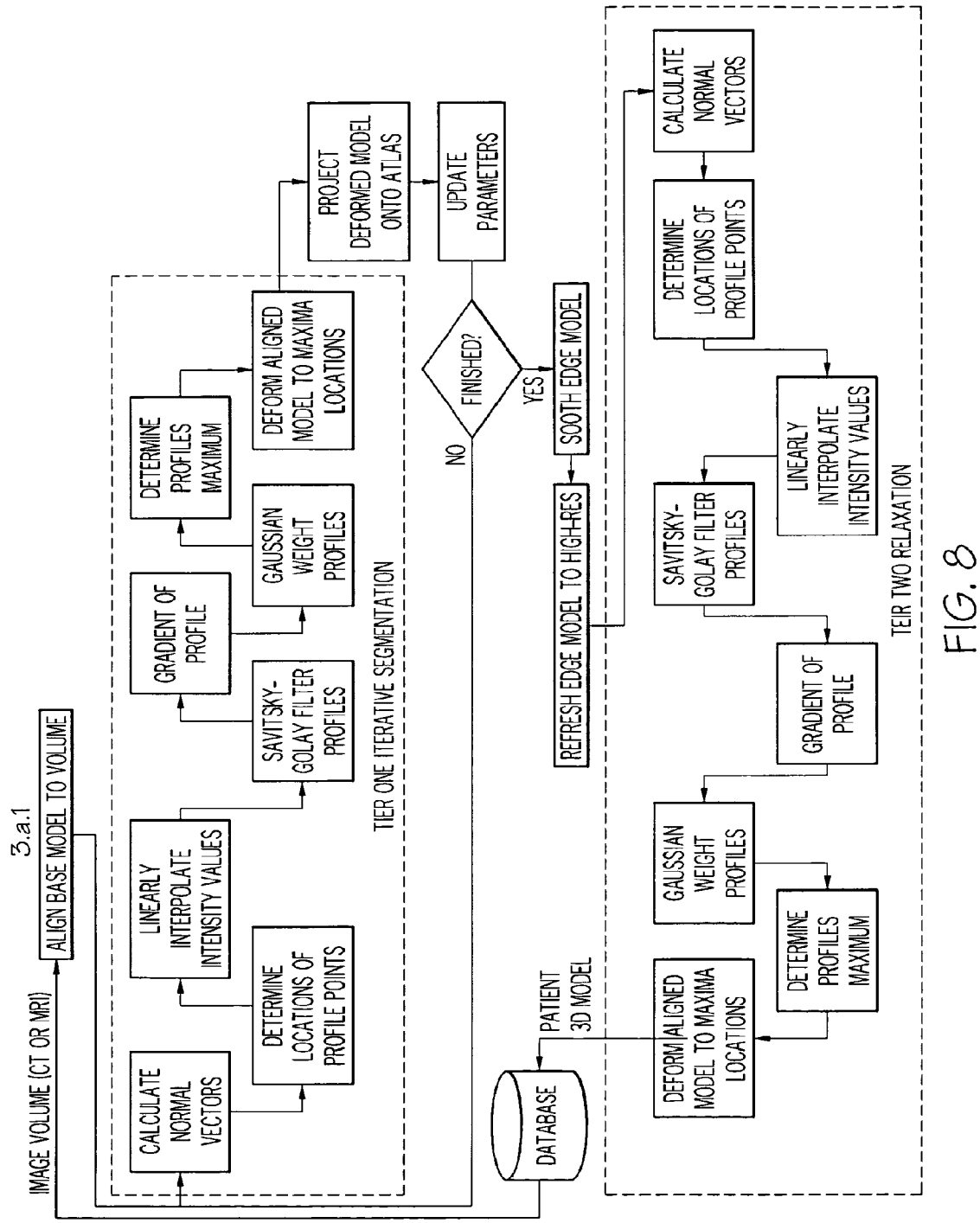
FIG. 8 is an exemplary diagram showing the processes of the algorithm for automatic segmentation within the segmentation process in accordance with the instant disclosure.

Automatic segmentation process is outline in FIG. 8. First step in segmentation process is aligning base mesh from statistical atlas with the volume an automatic alignment algorithm was developed to perform an accurate alignment. This alignment process 3.a.1 is outlined in FIG. 9. This process involves extracting isosurface via simple thresholding. The isosurface is basically a surface mesh generated from all of the bone-like tissue in the volume. The isosurface is noisy, and one can't distinguish separate bones. Extract features from the isosurface and the mean atlas model (this can be done earlier and simply loaded). These features could be, but are not limited to, crease, or crest lines FIG. 10, umbilical points, or any other surface descriptor. Match feature points on mean model to those on isosurface via nearest neighbor or other matching method. The results here will be noisy, meaning there will be several mismatches, but a subset will be correct. Using some robust fitting method, for example, the RANSAC algorithm or the least median of squares method, find the transformation that minimizes the en⁻ or between matched points while maximizing the number of matches.

Upon completion of the previous alignment step an iterative warping procedure which uses the information in the atlas as a constraint on the model's deformation is performed. The initial parameters determine the number of principal components to start with, the initial search length and the minimum allowed search length. The first step is to compute the vertex normals for each vertex on the bone mesh. These normal directions represent the direction of deformation for each vertex. These normals are calculated by averaging the normals of the adjacent triangles in the mesh. The search line for each vertex, defined by the normal direction, is the path extending inward and outward from the bone model, centered at the vertex. The length of the search line decreases as the process progresses.

Figure 11:
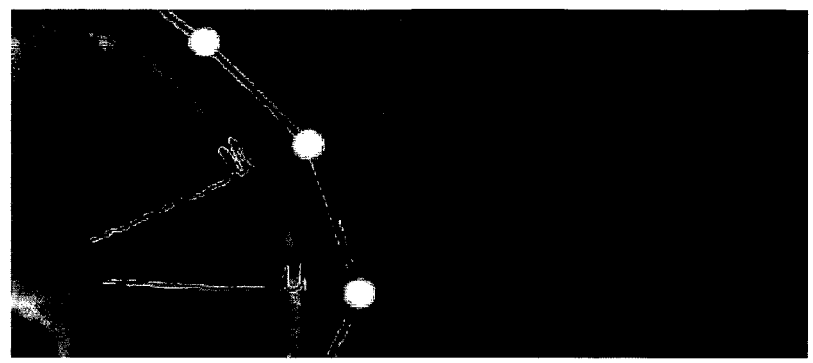
FIG. 11 is an illustration showing profile search along normal directions for CT.
Figure 12:
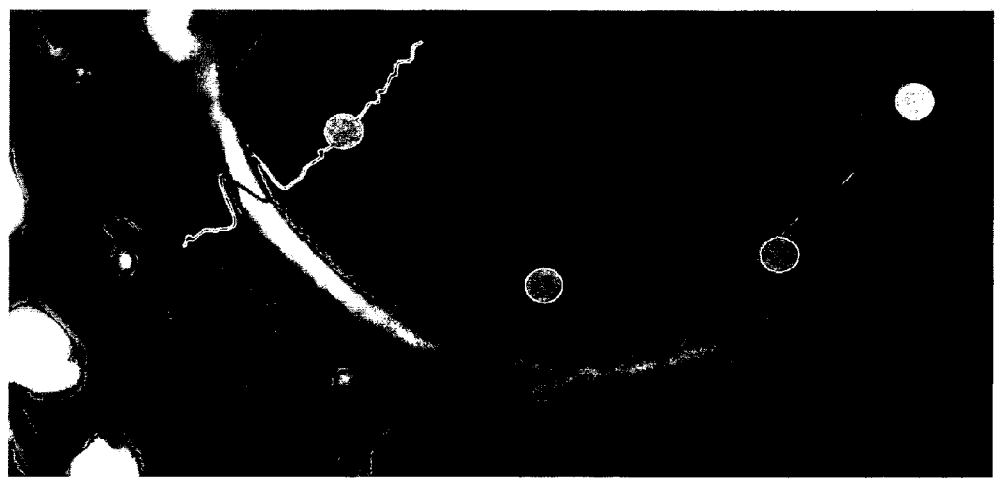
FIG. 12 is an illustration showing profile search along normal directions for MRI.
Figure 13:
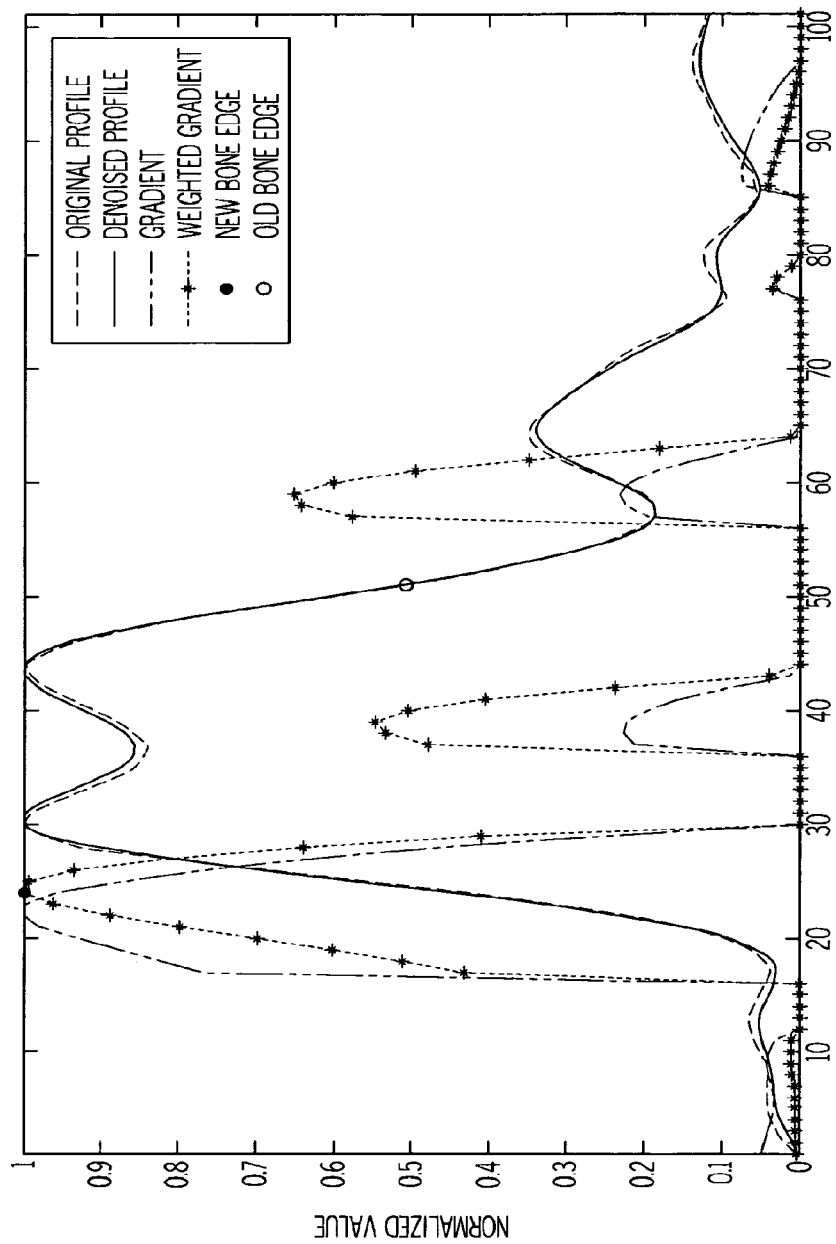
FIG. 13 is a graph showing the profile at various stages and the new edge location relative to the old edge location.

The intensity values for the search line are computed via trilinear interpolation, as the sampling rate of the search line can be higher than the given volume resolution. Profiles are first smoothed via some denoising filter, here we use Savitsky-Golay filtering. This is especially important given the noisy nature of MRI images. After denoising, the gradient along the profile is calculated. This initial gradient is insufficient to determine bone edge location as there are several tissue interfaces with strong gradients, such as the skin-air interface. This can be seen in FIGS. 11 and 12. As the initial automatic alignment is considered very accurate, it is safe to assume that the patient-specific bone edge is located near to the aligned vertex. To model this assumption, the gradient profile is weighted by a Gaussian function, so that the center vertex is given an initial weight of 1.0, with the weights decreasing as the search proceeds farther from the central position. An illustration of the profile at various stages can be seen in FIG. 13. After the weighting, the absolute maximum of the gradient is determined, along with its location. This location represents the bone edge; the old vertex location is then replaced with the new edge location.

Figure 14:
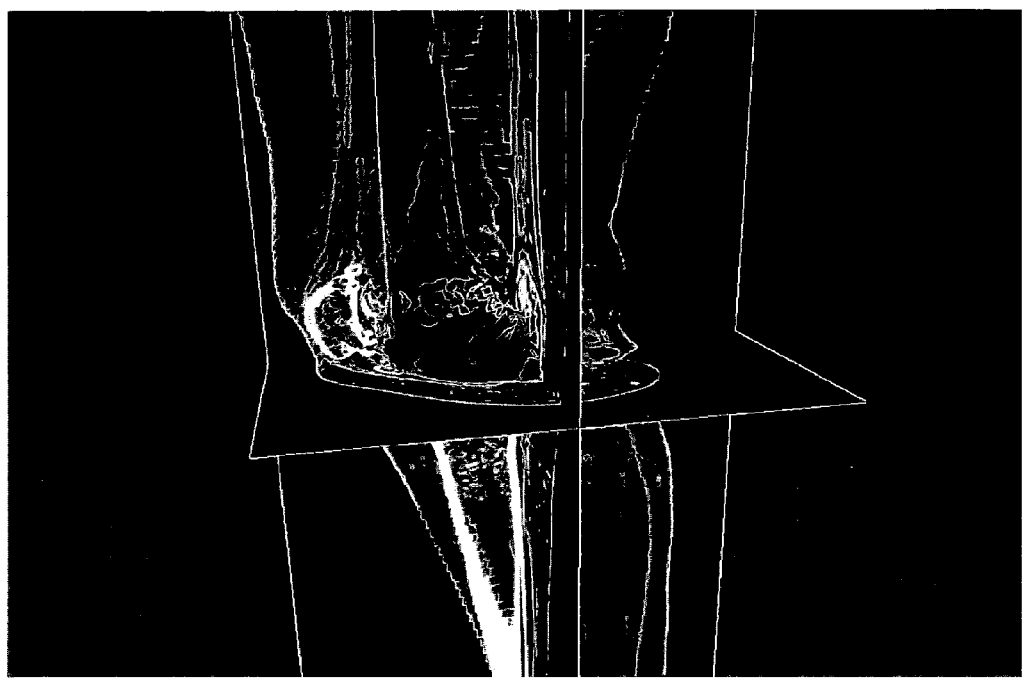
FIG. 14 is a segmented image with edge relaxation.

For CT the process seeks locations of falling edges, or edges that go from high intensity to low intensity as the search moves from inside to outside. The opposite is true for the MR case. Therefore, if necessary, the profiles are flipped before the steps above to account for modality differences. After the deformation for each vertex is performed the model is aligned with the atlas using the inverse of the transformation calculated in the initial alignment step. This model can be considered noisy, as some edge locations are located at incorrect positions. In order to constrain the deformation and remove as many noisy points as possible, we project the noisy model's vertices onto the atlas space using a specific number of principal components, which is determined by parameter that change based on the residual error as in FIG. 14. The resulting model will be a healthy femur which best represents the patient specific noisy model. These models are then transformed back to the volume space.

Figure 17:
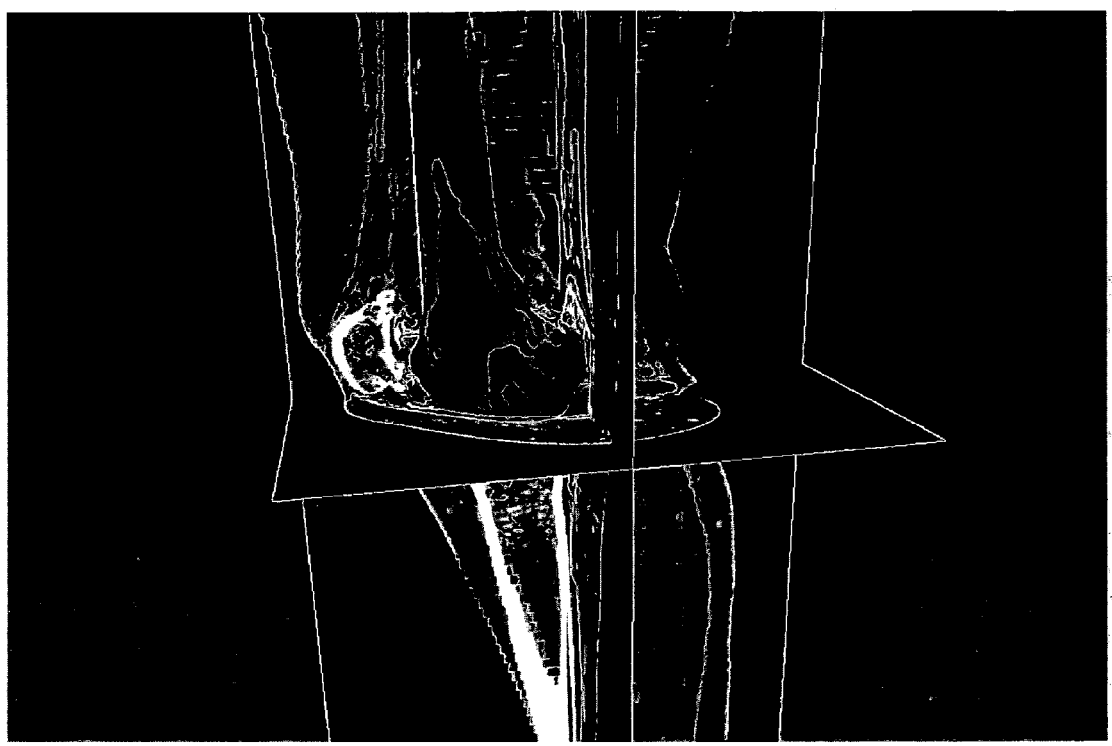
FIG. 17 is a segmented image after relaxation.

After projection, the parameters are updated, so that the search length is decreased, unless a new principal component is added. Then the search length is slightly increased so that new local information can be captured. A new principal component is added when the residual RMS reaches a sufficiently low threshold. The process above, starting with the normal direction calculation, repeats until all principal components are used and the residual RMS is sufficiently low, or until a set maximum number of iterations is reached. The resulting noisy model, contains the patient-specific information, is then smoothed and remeshed at a higher resolution[FIG. 15,16]. The higher resolution allows the capture of small local deformities, such as osteophytes, which may have been missed in the lower resolution segmentation process. The high resolution model is then relaxed by performing one iteration of the segmentation procedure, using a sufficiently small search length to prevent incorrect bone locations, stopping before the bone is projected onto the atlas. This resulting bone is a highly accurate representation of the patient anatomy. The output of the segmentation is then a high resolution patient-specific bone model and a smooth model, representative of the nearest healthy bone generated by the atlas before relaxation[FIG. 17].

After the automatic segmentation is complete we have 2 bones. The bone projected on the atlas, and the relaxed, patient-specific bone. If the bone is highly degenerative, we can perform an unconstrained relaxation using Gradient Vector Flow (GVF) snakes. These snakes respond to the gradient information present in the image and the flow of the gradient act as forces which cause the snake contour to locally expand or contract to the boundary that minimizes the forces on the contour. If the contour is not highly degenerative, then the initial relaxation step most likely is very near the actual patient anatomy and the snake method is not necessary. The snakes and interactive segmentation tools can be seen in FIGS. 7 and 8. The final segmentation step before model generation is an interactive intervention to correct any errors in the segmentation process. Several tools are provided for interactive segmentation, such as contour adding or subtracting, painting, etc. Once the segmentation has been confirmed, the final model is generated by interpolating the contours at a fine resolution to ensure a smooth result.

Figure 18:
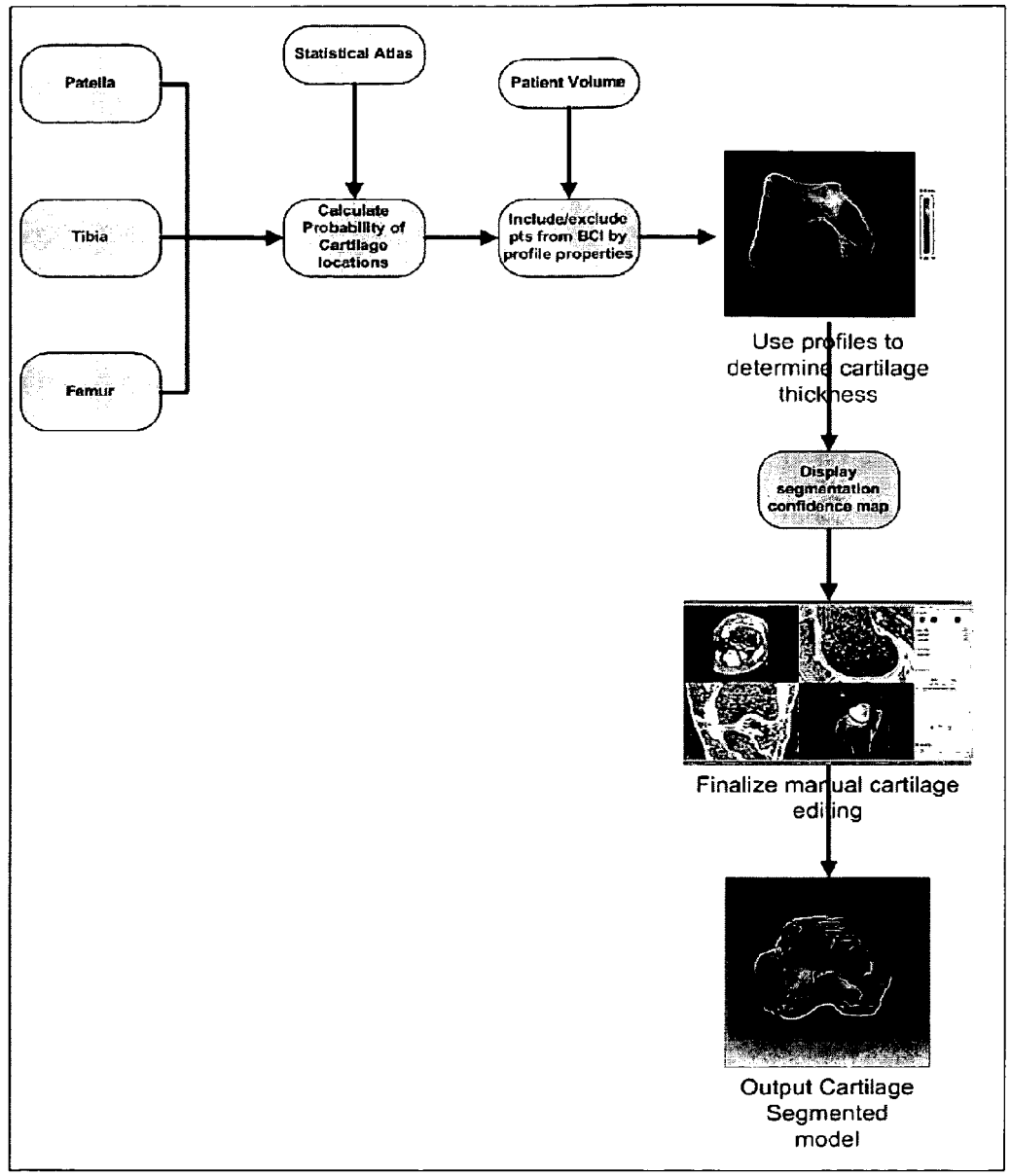
FIG. 18 is an exemplary diagram showing the process of cartilage segmentation from MRI.
Figure 19:
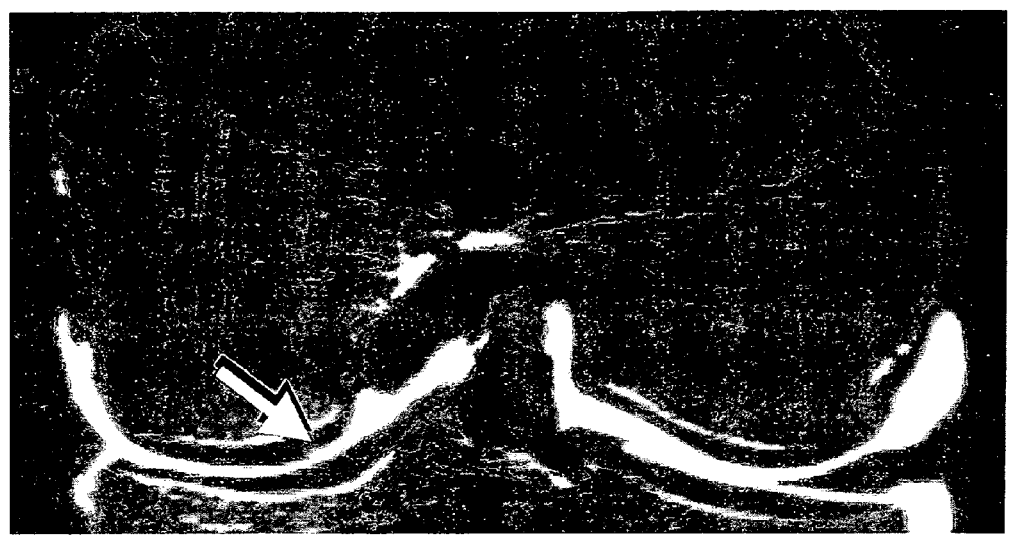
FIG. 19 is a CT image taken with a contrast agent that allows visualization of cartilage tissue.

The process of cartilage segmentation from MRI is shown in FIG. 18, upon patient volume segmentation, the resulting patient specific bone models of the distal femur, proximal tibia and patella can be used to acquire patient specific cartilage models. If enough information is present in the scan, which is the case when MRI is used or CT with a contrast agent (FIG. 19) that highlights the cartilage tissue, the cartilage can be segmented by utilizing a priori information along with measured patient specific information. The a priori information can be considered as a feature vector.

In the case of the cartilage this can be thickness or location information relative to the joint bones. The confidence placed in the a priori data is represented via the probabilistic models of each feature. For example, the confidence that the cartilage is x mm thick at a certain point on the bone is modeled in the cartilage thickness map built from previously segmented cartilage models. To determine the posterior probability, say, the cartilage thickness at a new point, a Bayesian inference model is used, of the form $$p(x|m) = \frac{p_{pr}(x)p(m|x)}{p(m)}$$

Here, p(x|m) is the posterior probability given m, the measurements. The value p(m|x) is the likelihood function representing the likelihood that a given measurement, m, would occur given a value of x. The p(m) term is a normalization term. The prior probabilities are present in ppr(x), the prior probability density. The best guess one can make for the value of x given some measurement in is then the x which maximizes the posteriori probability. This is known as the maximum a posteriori estimate (MAP). For cartilage thickness estimation (x), the MAP estimate is sought given the joint spacing (m) and the prior thickness map (ppr(x)). This same concept can be applied for BCI location.

Figure 20B:
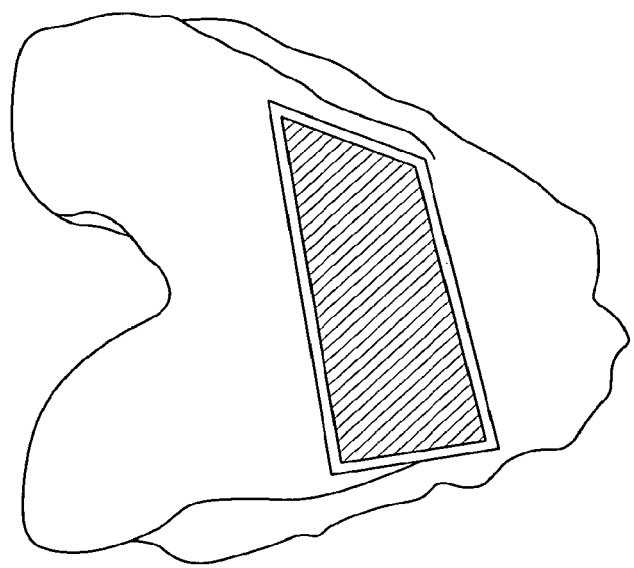
FIG. 20A and FIG. 20B are images of two femoral surfaces for profile computation, with image (a) including a tibia contact surface and image (b) including a tibia non-contact surface.
Figure 20A:
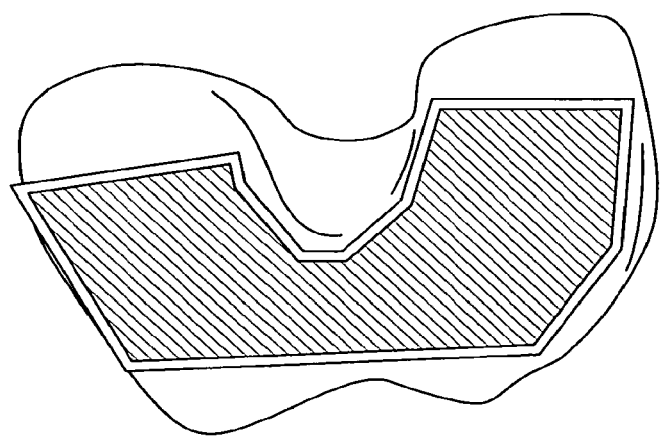

Initially, the search is limited to the articulating surface. This is done by utilizing the a priori information present in the atlas. The contact surface consists of the vertices in the atlas which are most likely to lie on the bone-cartilage interface (BCI) and which are near contact with an opposing bone. The non-contact surface is limited to those vertices which are likely to contain cartilage, but which are not in contact with a bone. These surfaces can be seen in FIG. 20.

Figure 21A:
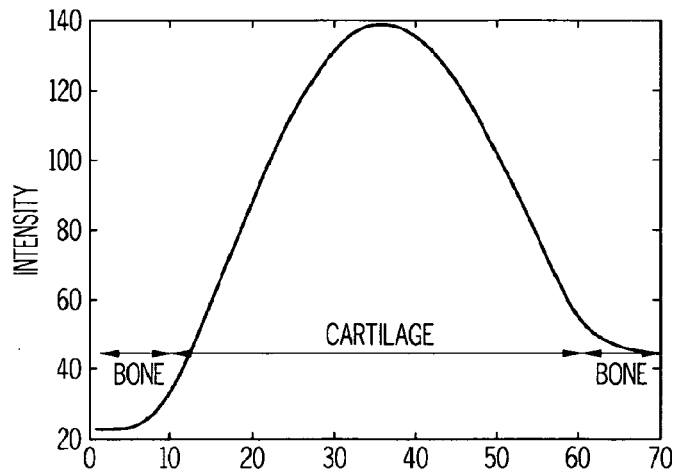
FIG. 21A, FIG. 21B, and FIG. 21C are mean profile graphs for class 1 (a), class 2 (b) and class 3 (c).
Figure 21B:
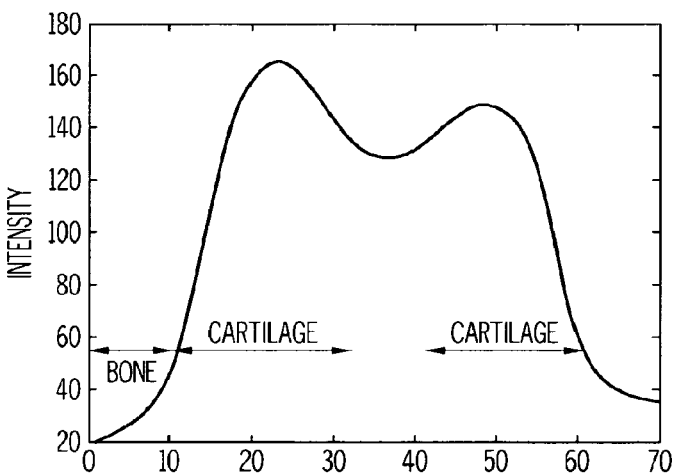
Figure 21C:
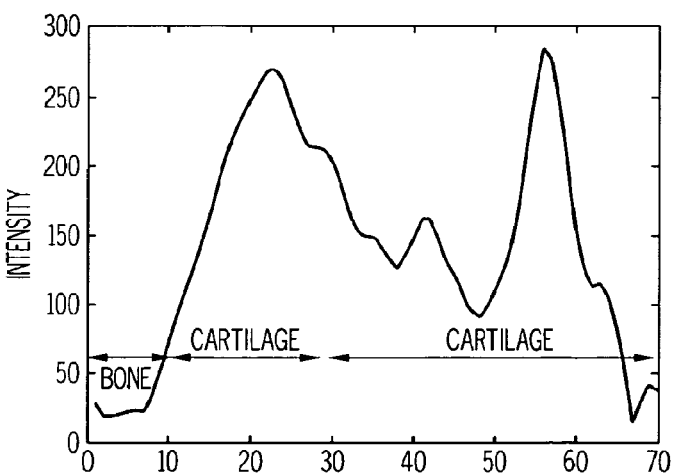

The profiles for each the contact surface are calculated along a path between the current bone's vertices and the nearest vertex on the contact bone. The profiles for the non-contact surface are calculated along the normal direction of the bone surface up to 1 cm. The local maxima and minima for each profile are calculated and the profiles are placed into one of three distinct classes. The mean profile for each class is shown in FIG. 21. If the profile contains a single maximum, it belongs to class 1. These are the shortest profiles and correspond to locations where the tibial and femoral cartilage are in close contact and are indistinguishable from one another. Profiles containing 2 maxima and one minimum are said to belong to class 2. These correspond to profiles of intermediate lengths where there is a clear space between femoral and tibial cartilage. Class 3 profiles are the longest profiles, where the femoral cartilage is usually well represented but the curves in class 3 vary widely and are often irregular.

Any vertex having a profile belonging to class 1 or class 2 can immediately be classified as belonging to the BCI. Class 3 profiles are added or subtracted from the BCI based if the intensity level is near that of other BCI points and the likelihood that the point belongs to the BCI, which is determined from the probability map of BCI.

After the BCI has been automatically determined the user is presented with the option for manual confirmation, and can edit the BCI using a number of tools similar to those found in the bone segmentation editor. When the BCI is determined to be sufficiently accurate the segmentation of the cartilage model proceeds. The cartilage is segmented along the profile dimensions using gradient information from the scan volume coupled with the a priori knowledge of the cartilage thickness. This a priori knowledge provides an initial estimate of the likely cartilage edge, which is then updated by seeking the local maximum of the absolute value of the profile gradient. For class 1 profiles, the cartilage edge is considered to be at the local maximum. For class 2 and 3 profiles, the local maximum of the gradient is used.

Figure 22:
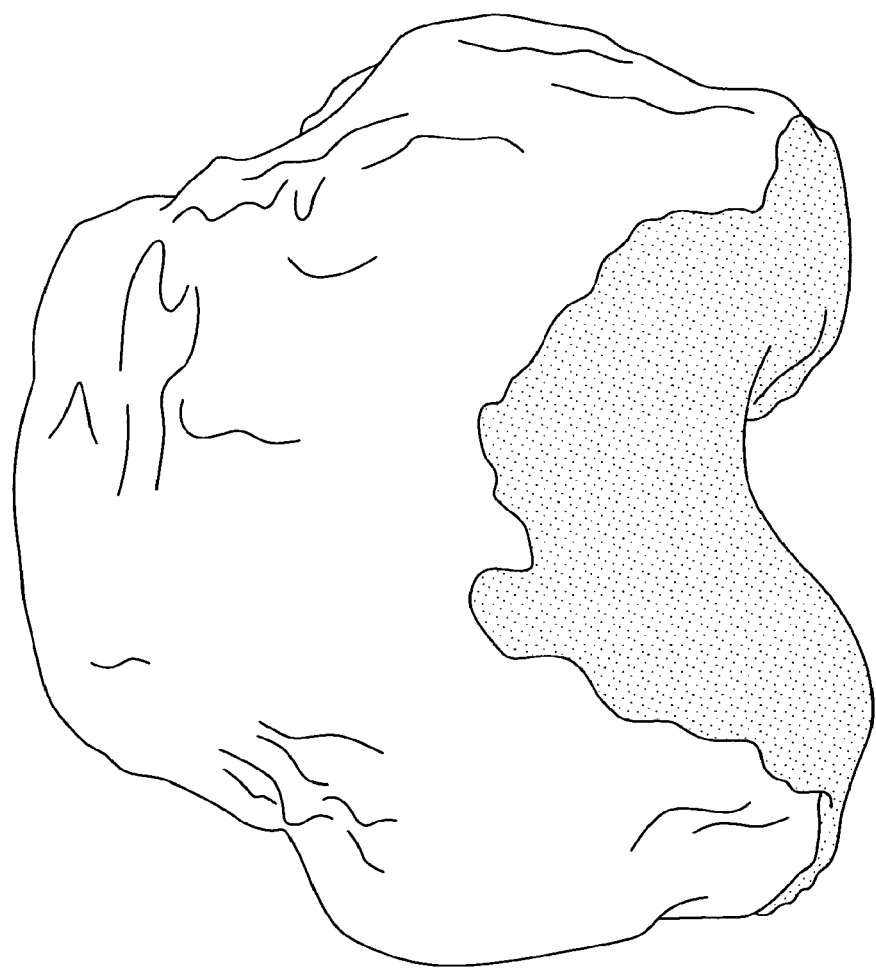
FIG. 22 is an image of a segmented bone and cartilage from MRI.

The cartilage segmentation can then be interactively adjusted if necessary before the final cartilage model is output. Segmented femoral cartilage can be seen in FIG. 22.

Figure 23:
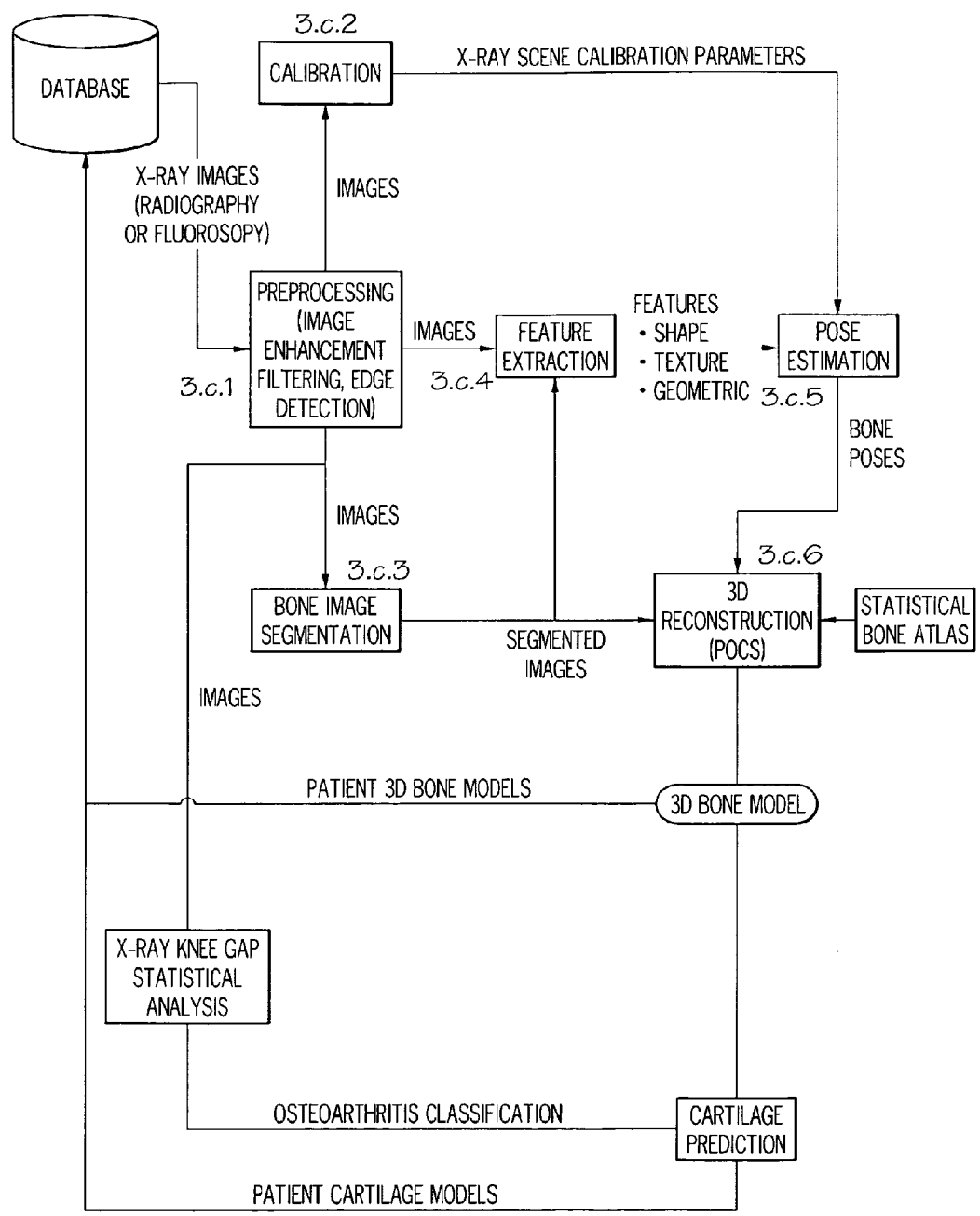
FIG. 23 is an exemplary diagram of an X-Ray 3D model reconstruction process flow.

X-Ray bone reconstruction process is outline in FIG. 23.

X-Ray Images are taken using either traditional fluoroscopy or radiography. The number of images can be either one or more. The image(s) projection view is taken to maximize the obtainable information by scanning at large angle differences. Accuracy of the system is directly proportional to the number of images, while speed is inversely proportional. Radiographic scene properties focal length and image resolution (of camera digitizer or film scanner) are manually input to the system if not readily available in the image's file header.

The goal of preprocessing is to enhance the input images by reducing image noise, increasing image contrast, and preparing the images for further analysis. This would be automatically done, with the possibility of manual intervention for extreme image distortions. Gaussian, median and Sobel filters will be used.

Figure 25:
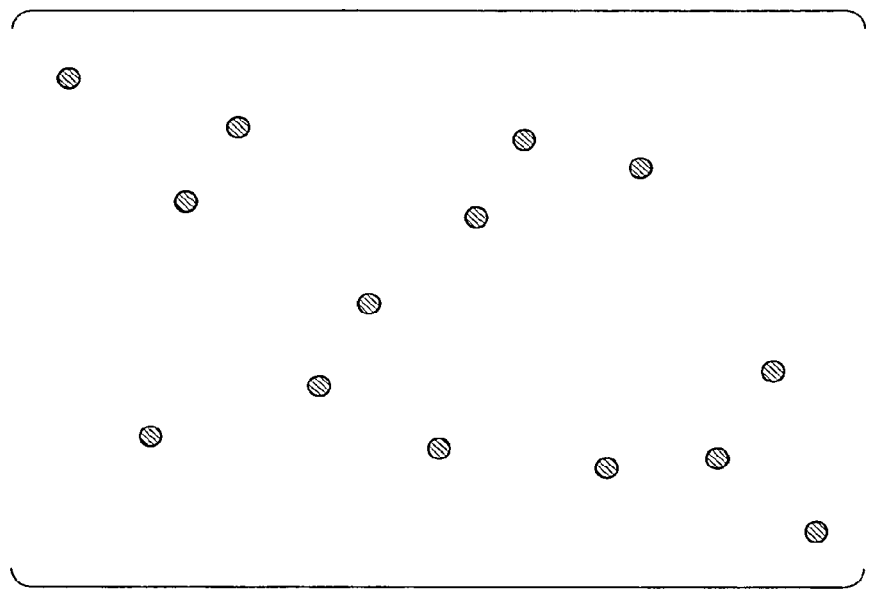
FIG. 25 is an exemplary image showing beads as would appear on a radiographic image.
Figure 24:
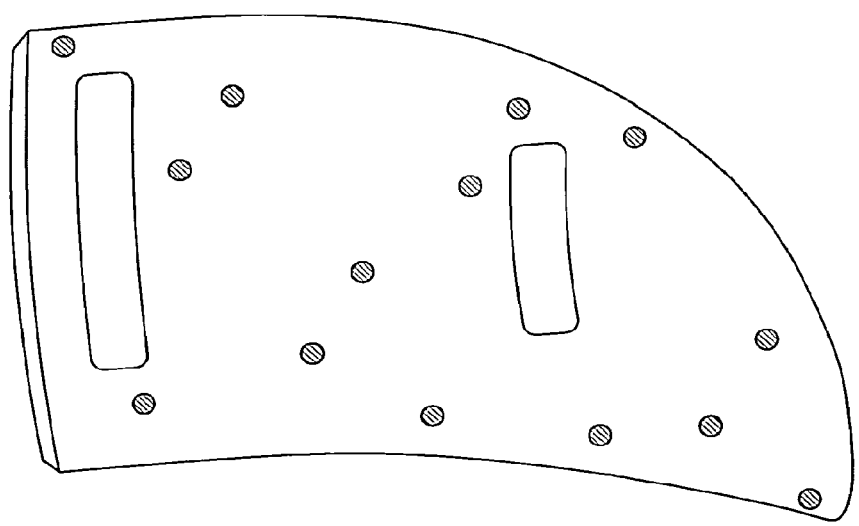
FIG. 24 is an image of an exemplary calibration target.
Figure 26:
FIG. 26 is a radiograph of the leg with the calibration target attached.

Calibration involves the extraction of the imaged bone pose within the radiographic scene. Before image acquisition, a calibration target is attached to the patient's leg [FIG. 24]. This target would contain radio opaque beads that would appear on the acquired images[FIG. 25,26]. The bead projections would be automatically extracted from the images and used to roughly estimate the bone pose relative to the x-ray source.

The markers can then be automatically detected in the images using morphological operations. The placement of the markers on the subject is chosen to cover as large an image area as possible in all the frames. Enough markers were used to allow accurate pose estimation even when the feature detection algorithm missed some of them, or when some of them were outside the field of view.

By thresholding at various levels and removing (with morphological operations) any objects that contain lines longer than the bead diameter, we can isolate these beads. We find the centroids of the beads by finding the connected components and then determining the centroid of each component. The calibration target is designed to minimize possible overlap of bead projections, which maximizes the number of detected beads.

The pose of the sensor is computed by finding correct associations (or correspondences) between the detected bead locations in the image and the 3D bead locations. This is accomplished using an interpretation tree search method. In this method, each level of the tree represents the correspondences between an image point and all possible model points, and each path from the root to a leaf node in the complete tree represents one possible correspondence. When a search descending the tree reaches a node at which at least four correspondences have been hypothesized, the correspondences are used to calculate a pose solution. In general, we only need three points to solve for a pose, but there may be more than one solution since three points are always co-planner. We require that at least four points be used.

Once we have four correspondences we can calculate a pose. This pose solution is used to project the object points back onto the image for comparison to the detected markers as a measure of how well this solution fits the complete data set. If the pose solution fits the data well then the correspondence and computed pose are correct. If the pose solution does not fit the data, then the correspondence is wrong, and the tree is traversed further to check additional correspondences. Since for a large number of points this tree may be very large, we do not search the entire tree. In fact, we search the tree further only if the current correspondence produces an error larger than some threshold. If it is below, we assume we have found a correct correspondence.

Once the correct correspondences have been found, we compute the pose using a non-linear least squares method. Specifically, given an image point P, a 3D model point Q, and the six-vector containing the correct pose parameters $\beta$, let the transformation to project onto the image be given by the function $f(\beta, Q)$ such that $P=f(\beta, Q)$. The vector function $f$ also represents a perspective projection (whose parameters are known from calibration). Linearizing around a current pose solution $\beta$ we get $$\Delta P = \left(\frac{\partial f}{\partial \beta}\right)\Delta\beta.$$

Given at least four point correspondences, we can solve for the correction term $\Delta\beta$. This process is iterated until the solution converges. The final solution is the pose $\beta$ that minimizes the squared Euclidean distance between the observed image points and the projected model points on the image plane.

Figure 27:
FIG. 27 are segmented images of a distal femur.

The bone image segmentation block takes the preprocessed images as input. Its goal it to extract the actual bone contours of the all the images. This is done automatically using a statistical atlas of bone contours generated using our database of 3D bones. A template average bone contour from the statistical atlas is initially placed within the image, and then translated and rotated to align with the bone's image. After that, contour deformation is statistically done to fit the target bones image based on the image's intensity values and edges obtained from the preprocessing step. Manual and semi-automatic contour editing tools are also available for the verification of the automatic process [FIG. 27].

The feature extraction module is responsible for the extraction of image parameters from the images. These parameters are extracted from both the preprocessed and segmented versions of the images. Types for features include information extracted from the segmented bone contour (curvature, geometry, aspect ratio . . . etc) or from the pixel intensity values (texture features such as Haralick and Tamura's texture features).

This process is required because the calibration block is expected to introduce an error due to the relative transformation between the calibration target and the actual bone. In the case of fluoroscopy, the number of bone images is usually large and the bone pose difference between coherent images is usually very small. Therefore, we will apply pose tracking using particle filters.

This approach has been found to be useful in dealing in applications where the state vector is complex and the images contain a great deal of clutter. The basic idea is to represent the posterior probability by a weighted sampling of states, or particles. Given enough samples, even very complex probability distributions can be represented.

As measurements are taken, the weights of the particles are adjusted using the likelihood model, using the equation:

$$w_j^i = P(y_i|x_i)w_j$$

where $w_j$ is the weight of the $j^{th}$ particle.

Figure 28:
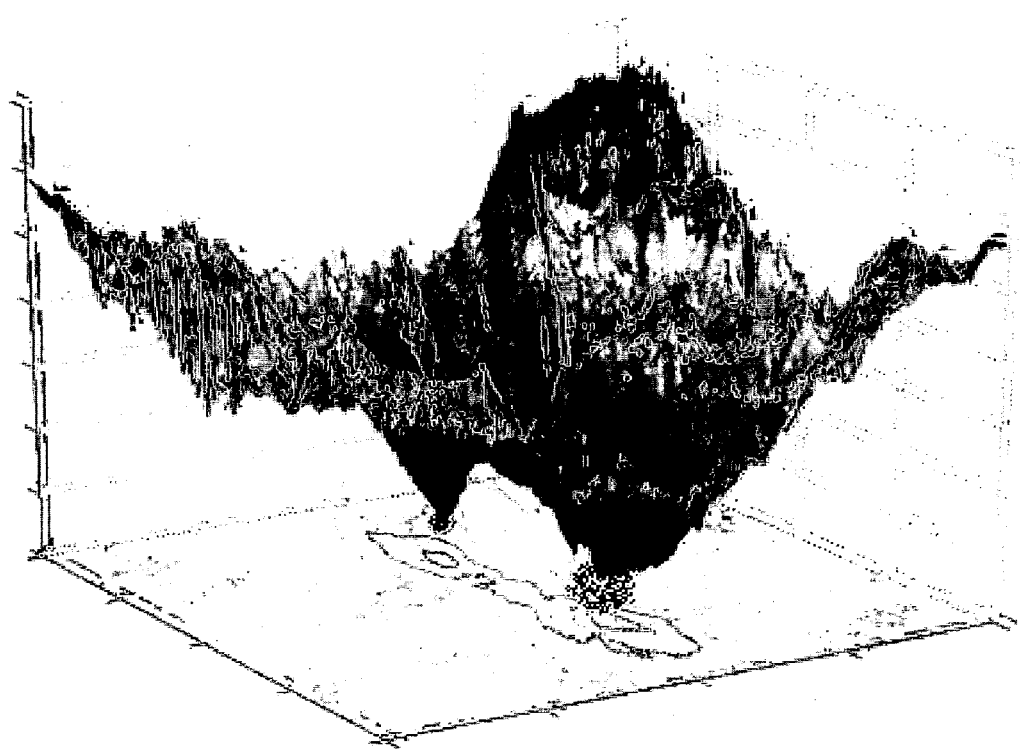
FIG. 28 is an image showing a complex pose search space and how particle filters succeed in finding the optimum pose.

The principal advantage of this representation is that it can represent multiple peaks in the posterior probability distribution, given enough particles [FIG. 28].

As measurements are obtained, the tracking algorithm adjusts the weights, and when enough data is obtained to disambiguate the states, eventually one of the particles has a high weight and all the others have very small weights. Another advantage of this approach is that it can determine when a unique solution has been obtained.

Resampling the particles. It is important to make sure that the sampling of states adequately represents the posterior probability distribution. In particular, we want a number of the samples to be close to peaks, where the weights are large. To ensure this, at each step we will resample the probability distribution by generating additional particles near large peaks, and discarding particles with very small weights. We will use importance sampling to inject samples based on bottom-up information.

Design of the likelihood function. It is important to design the likelihood function so that it is as smooth as possible. If it had many narrow peaks, some of those peaks could be missed unless a very large number of samples is used. The key is to use a similarity measure that has broad support for each hypothesis. In other words, the similarity measure should gradually grow as our hypothesized state gets closer and closer to the correct state, and not increase suddenly.

In the case of radiography, the number of images is usually limited, therefore, the features would be used in a Bayesian network framework where the expected output in the bone's pose given the current set of image features. This method can also be used to initialize the particle filter in case of fluoroscopy. The Bayesian networks would be constructed as directed acyclic graphs, where each node represents an image feature and node connections represent the conditional dependencies. The output is the pose with the highest probability, given the set of input image features. The network output probability is based on the probabilistic chain rule $$p(x_1, x_2, x_3, \ldots, x_n) = \prod_m^n P(x_m | x_{m+1}, x_{m+2}, \ldots, x_n)$$

Where $x_1$ $x_n$ represent the image features and bone poses variables.

Figure 29B:
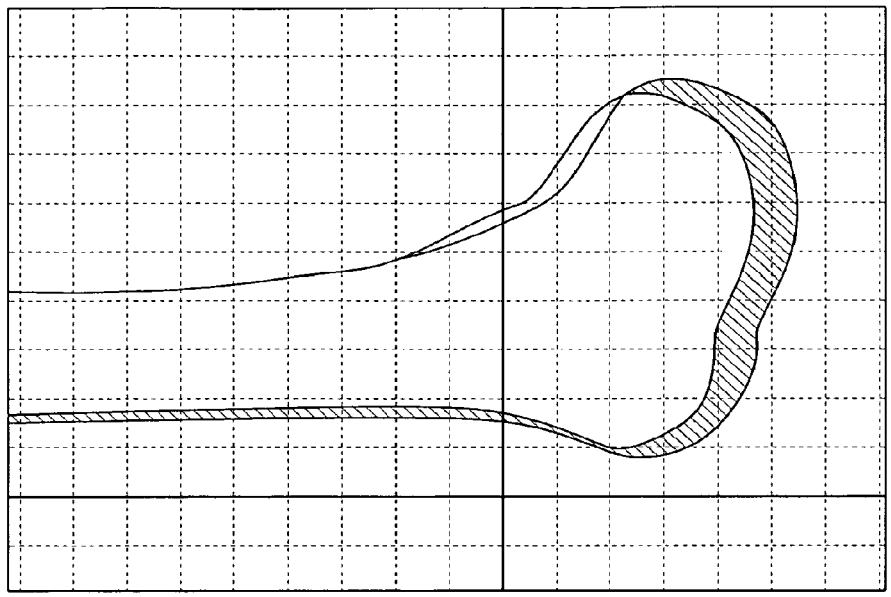
FIG. 29A and FIG. 29B are images showing the template bone's projection on the radiographs.
Figure 29A:
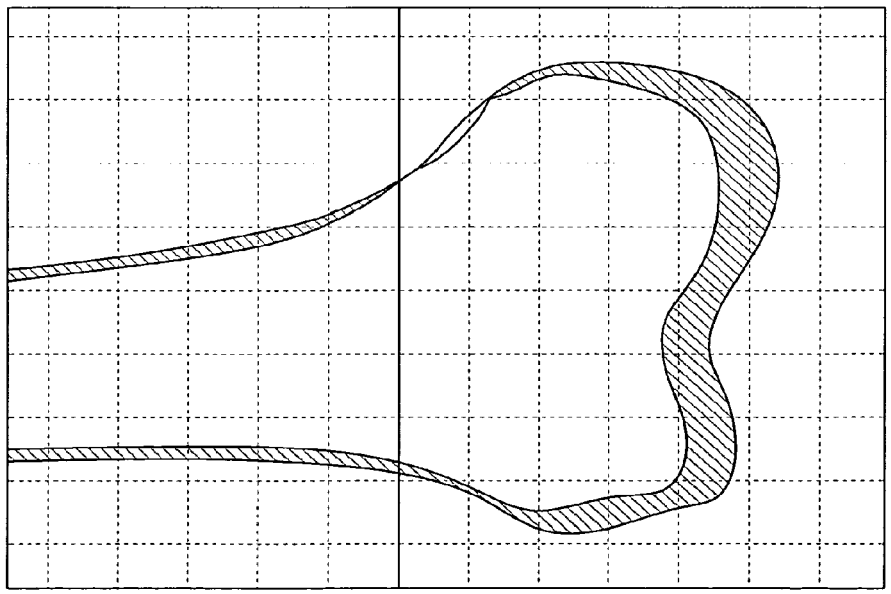

We use a 3D reconstruction algorithm based on GPU rendering simulation. The input for our method is the set of segmented images and their corresponding bone poses. The number of images and the variety of projection poses indicates the amount of information that can be obtained about the bone shape, hence the accuracy of the output. For each of the input images, a graphical rebuild of the radiological scene used to take the image is done. The x-ray source is represented by a perspective camera setup to simulate the radiological beam divergence. Within the camera's field of view, a template bone model is placed at a pose mimicking the actual bone's pose within the radiological scene[FIG. 29].

Figure 30:
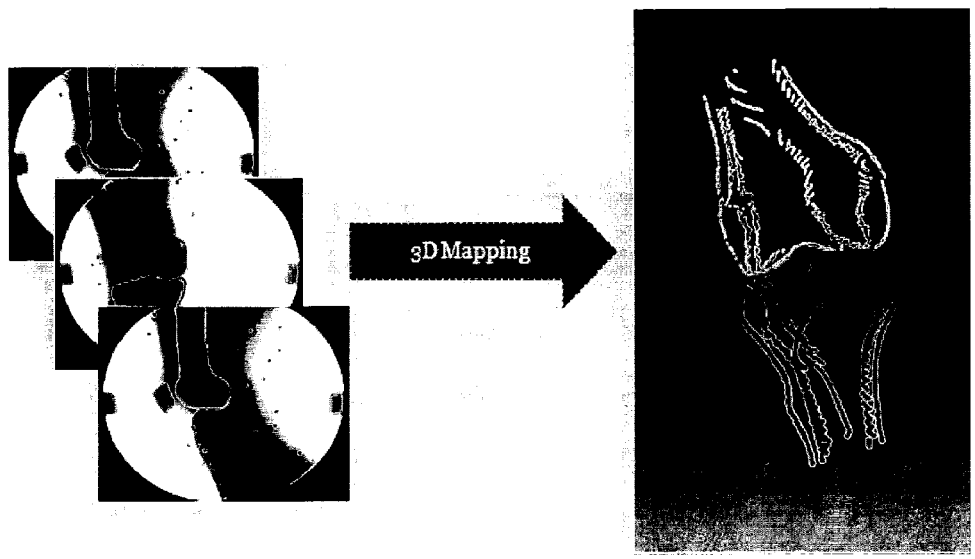
FIG. 30 are images of contours mapped to 3D.
Figure 31:
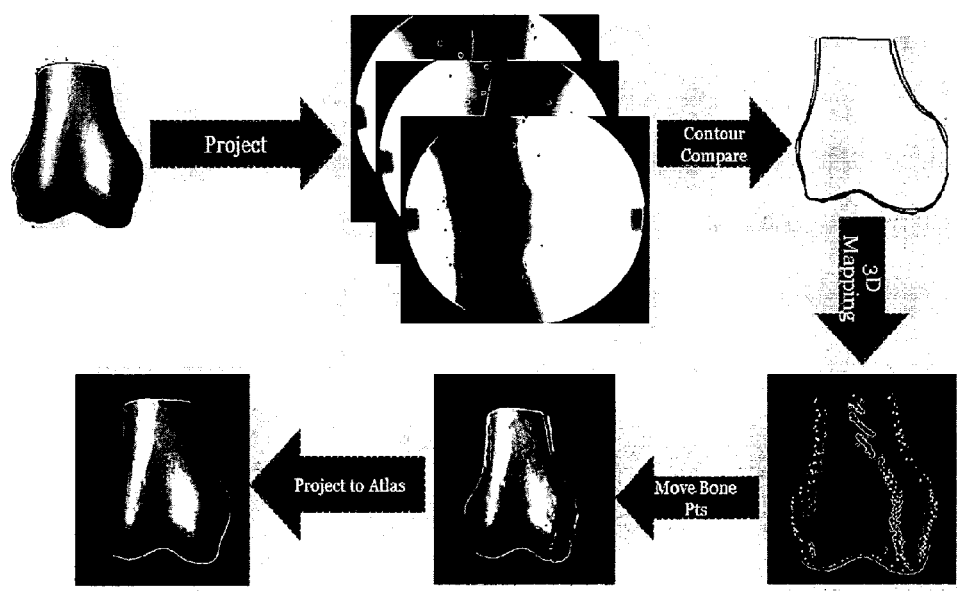
FIG. 31 is an exemplary diagram showing a 3D reconstruction process.

Having setup the graphical scene, bone projection images are synthesized, whose contours are mapped to 3D points on the template bone's surface by utilizing depth mapping rendering capabilities [FIG. 30]. These 3D points are then systematically translated in space to eliminate the 2D contour error between the synthesized image and the original radiographic image. As a result, using contour data from all images, a cloud of 3D points that would produce the bone projections similar to those of the input x-ray images will be produced [FIG. 31].

This transforms the problem to a 3D to 3D optimization problem. We will use POCS (alternating Projection On Convex Hulls) method to quickly and uniquely find the best shape that is consistent with both the statistical atlas as well as the generated point cloud. POCS is a powerful tool that has been used successfully for many signal and image restoration and synthesis problems. It is particularly useful in ill-posed problems, where the problem can be regularized by imposing possibly nonlinear convex constraints on the solution set. Iteratively projecting onto these convex sets results in a solution that is consistent with all the desired properties. A short description of the method follows.

In a vector space, a set p is convex if and only if for $\forall x \in \rho$ and $y \in \rho$, then $\lambda x + (1-\lambda)y \in \rho \forall 0 \le \lambda \le 1$. In other words, the line segment connecting x and y is totally subsumed in $\rho$. If any portion of the chord connecting two points lies outside of the set, the set is not convex A projection onto a convex set is defined as follows. For every closed convex set, $\rho$, and every vector, x, in a Hilbert space, there is a unique vector in $\rho$, closest to x. This vector, denoted PCx, is the projection of x onto $\rho$. The most useful aspect of POCS is that, given two or more convex sets with nonempty intersection, alternately projecting among the sets will converge to a point included in the intersection.

Figure 9:
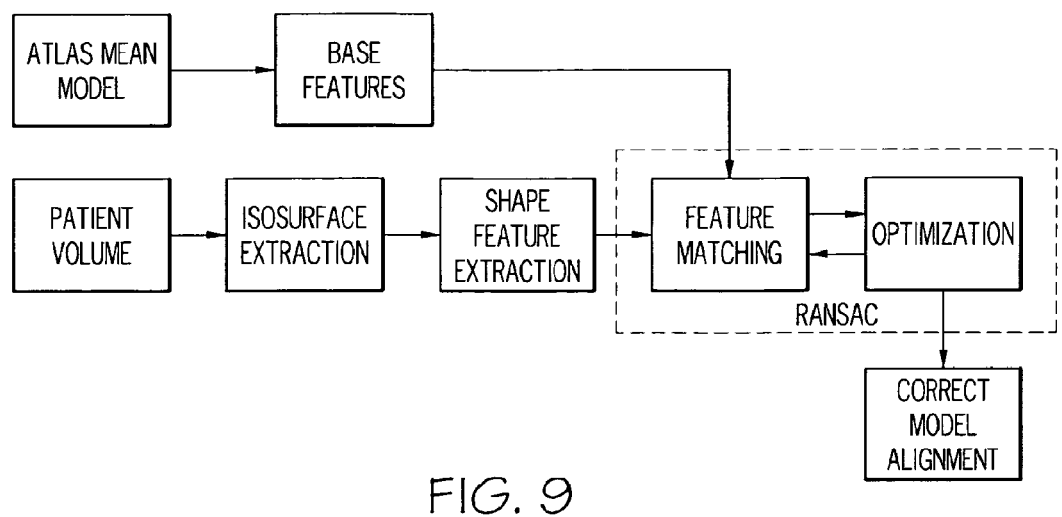
FIG. 9 is an exemplary diagram of the processes of an automatic alignment algorithm in accordance with the instant disclosure.
Figure 10:
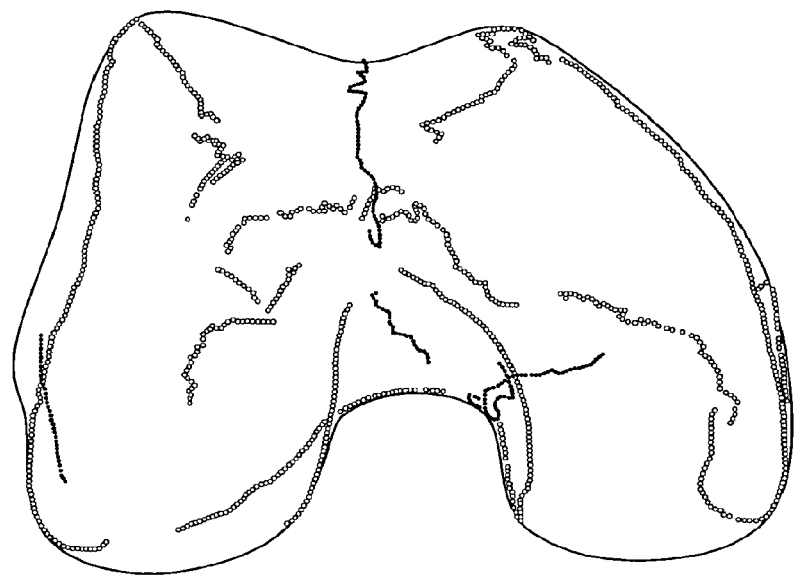
FIG. 10 is an illustration showing calculated crest lines as an example of the feature extracted from mesh for a distal femur.

If two convex sets do not intersect, convergence is to a limit cycle that is a mean square solution to the problem. Specifically, the cycle is between points in each set that are closest in the mean-square sense to the other set (FIG. 9).

In our method, we have two convex sets: 1. The set of all bones that can belong to the statistical bone atlas. 2. The set of all bones that have constrained values for a selected number of vertices (the other vertices can have any values). The selected vertices are those for which we see corresponding points on the image contour. We can project a bone vector onto the second set by simply replacing each of the selected vertices with the corresponding estimated point.

By alternating the projection onto one convex set and then the other, we will quickly converge to a solution that is compatible with both sets.

Having obtained a patient-specific bone model, cartilage should be added to complete the fitting surface where the jig should fit. Using our database of x-ray images, and their corresponding MRI scans, a Bayesian network was created that identifies the level of cartilage deterioration from the knee gap distance profiles of the x-ray images. Such information is used as an input to the cartilage generation module.

System includes a smart database that stores patient information following HIPPA regulations. Data from different imaging modalities will be attached with each patient including DICOM from MRI/CT, X-ray images, and ultrasound. Reconstructed bones and cartilage are stored in the database. Virtual templating data including calculated landmarks, axes, implant sizing, and placement information are also stored in the database. This component implements both relational and XML schema to provide a powerful tool for data storage and manipulation.

Figure 32:
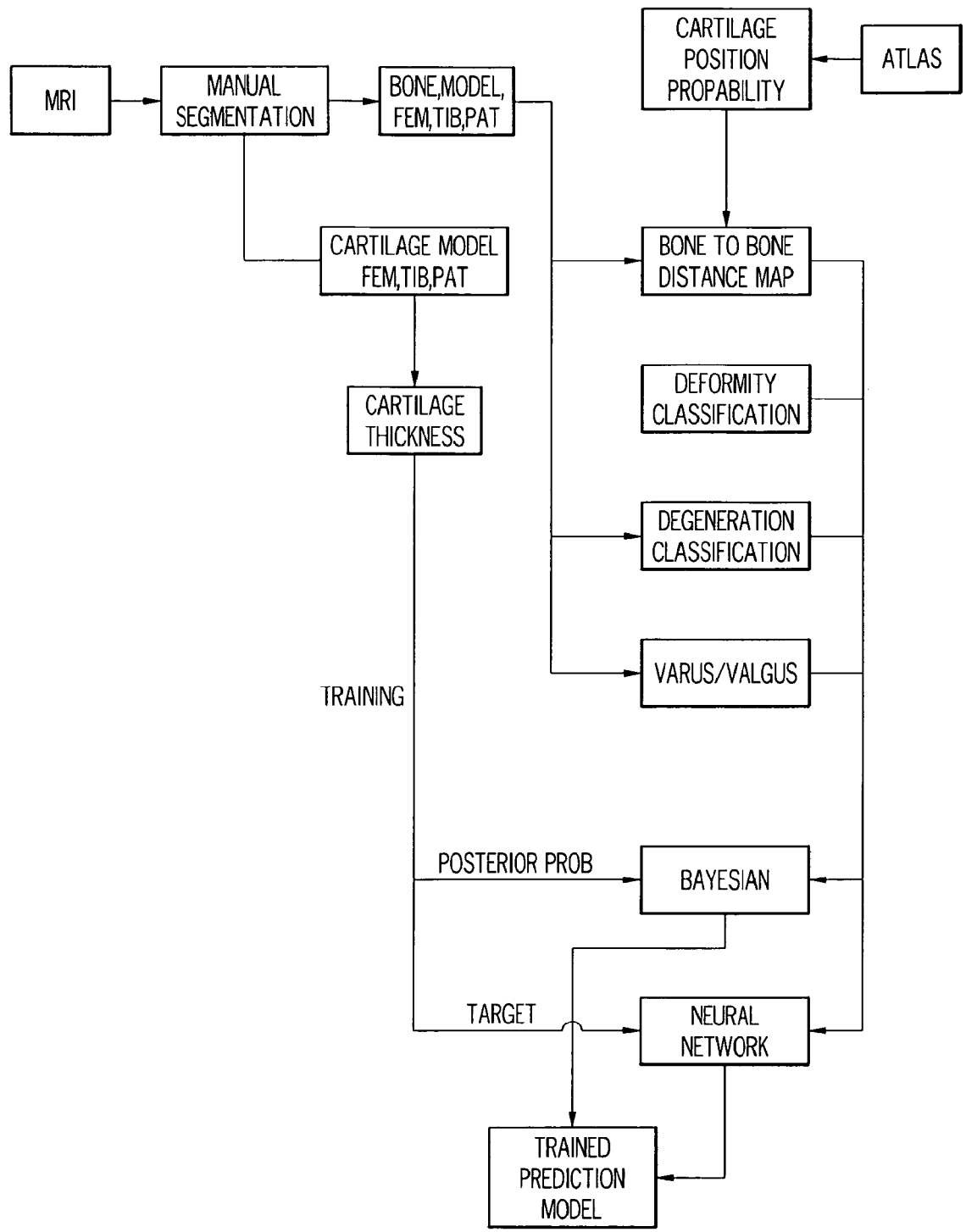
FIG. 32 is an exemplary diagram for training the prediction model for cartilage thickness.
Figure 33:
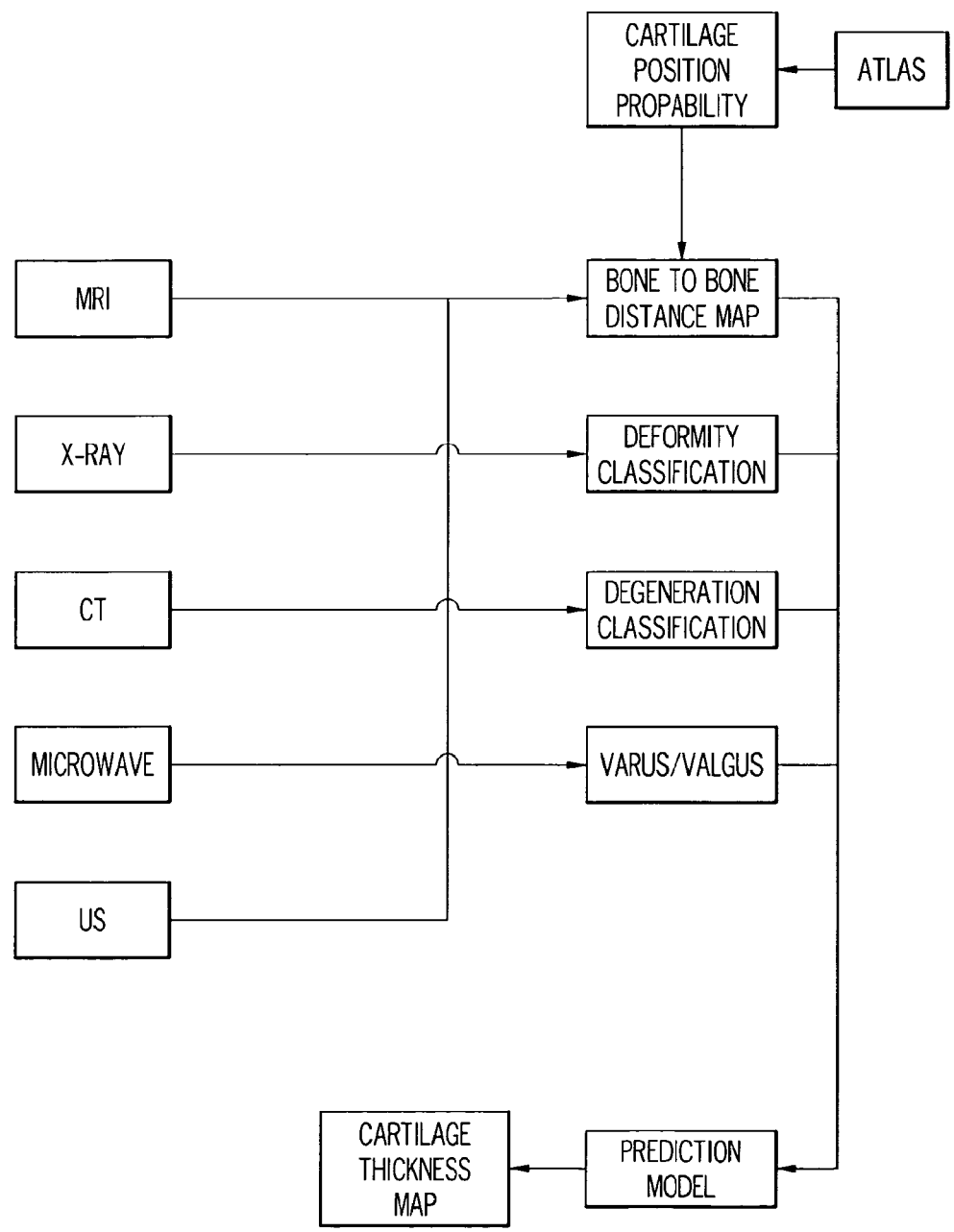
FIG. 33 is an exemplary diagram for cartilage reconstruction using trained prediction model.
Figure 34:
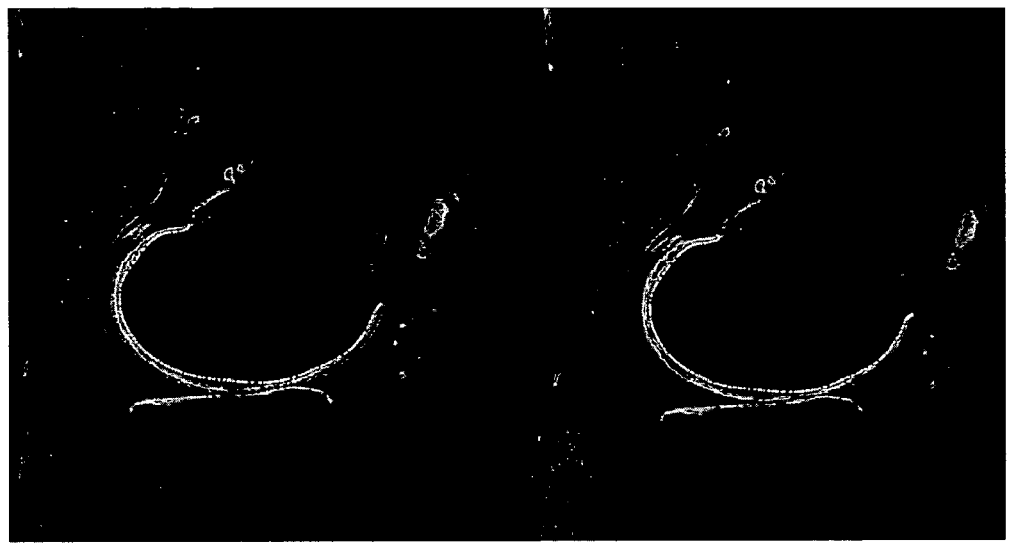
FIG. 34 are images of estimated cartilage thickness from MRI.
Figure 35:
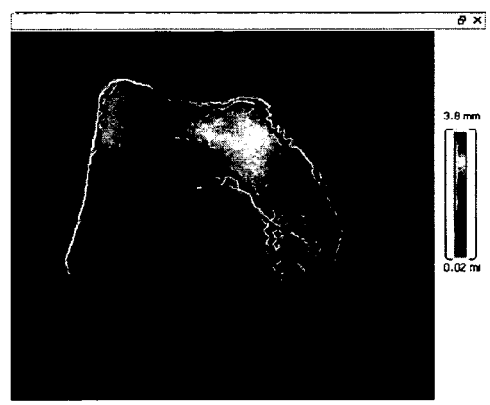
FIG. 35 is an exemplary cartilage template thickness map.
Figure 36:
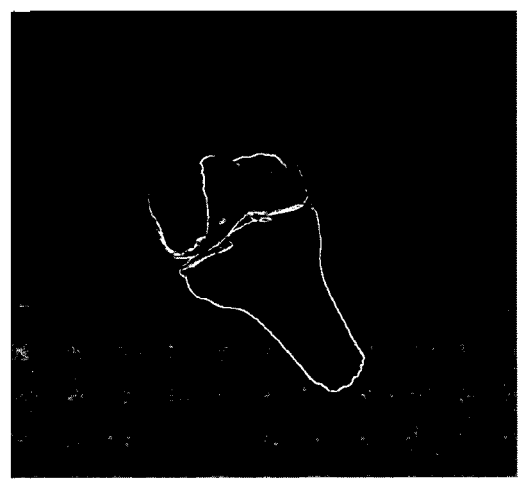
FIG. 36 is an exemplary image of predicted cartilage on a femur and tibia.

FIG. 32 outline the process of creating a prediction model for reconstructing the articulating cartilage given the femur, tibia and patella bone. To build this model we utilized a database of 2000 MRI scans. Bones and articulating cartilage were first segmented from these scans. Bones were added to our statistical atlas to achieve point correspondence and calculate the probability of bone cartilage interface areas on each bone. Bone to bone distances were calculated across the bone cartilage interface areas by finding the closest distance between the two bone surfaces at each vertex. Cartilage thickness were also calculated at each of these location and used as a target to train a neural network and construct a Bayesian belief network to predict the cartilage thickness. Input for these system included and weren't limited to the bone to bone distance, degenerative and deformity classification of the knee joint, and measurement of the yams and valgus angle. Output for this is a prediction system that's capable of constructing cartilage in CT, X-Ray, US, Microwave and to guide cartilage segmentation in MRI [FIG. 33]. FIG. 34 shows process of identifying cartilage interface in MRI training datasets, whereas FIG. 35 shows the average cartilage map. FIG. 36 shows output for the prediction model for one of the test cases.

Figure 15:
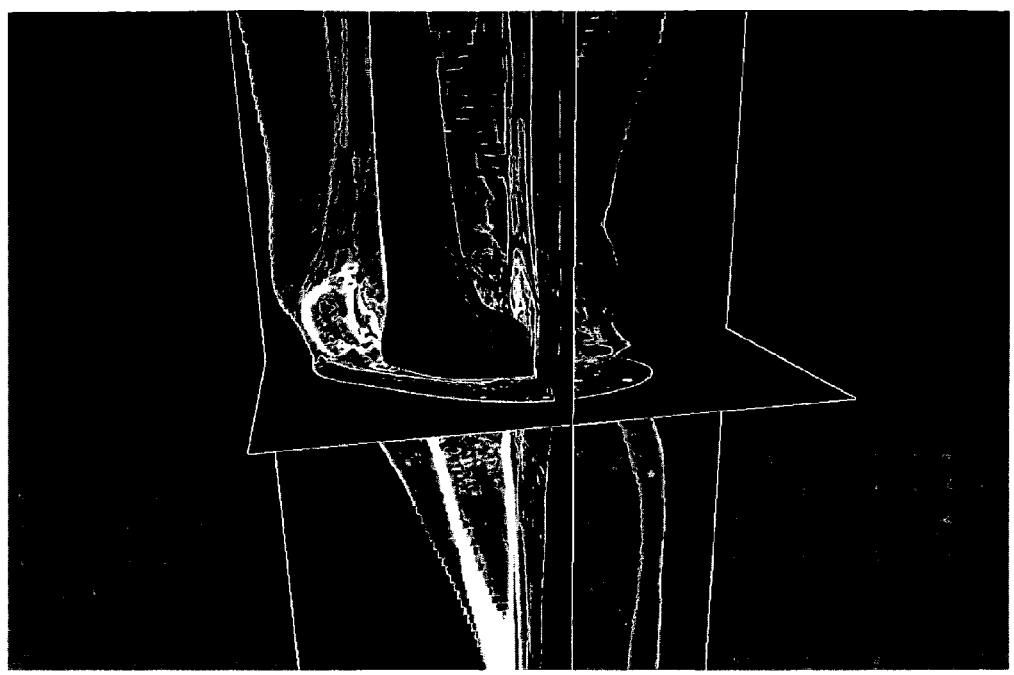
FIG. 15 is a segmented image.
Figure 16:
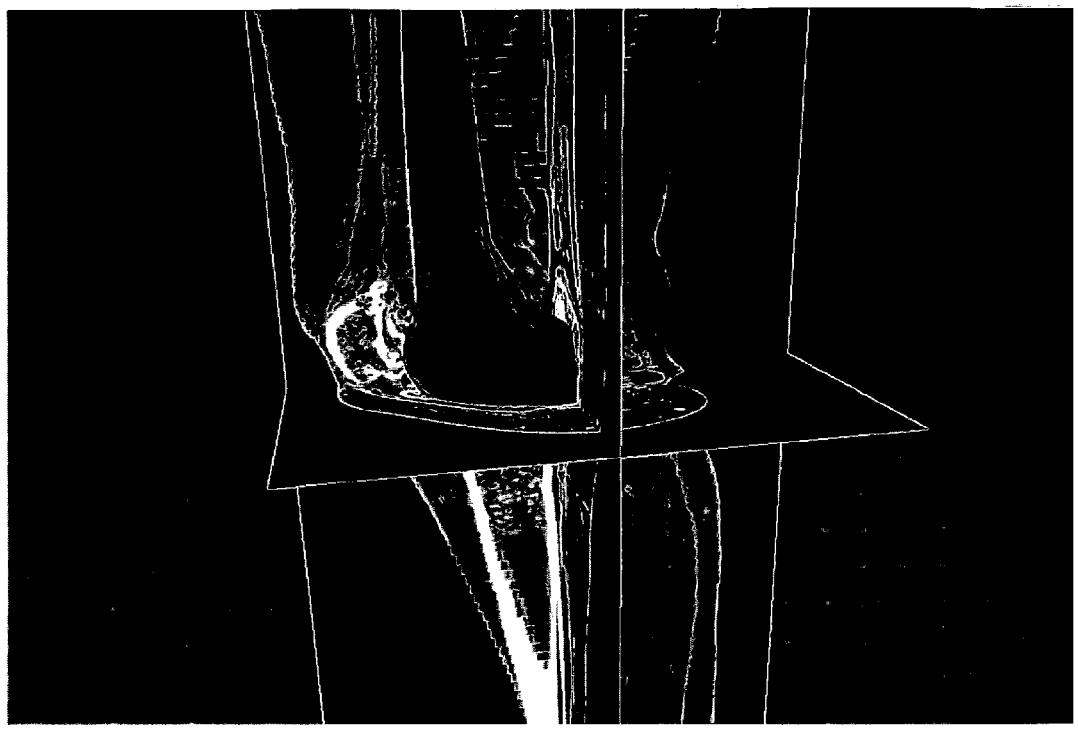
FIG. 16 is a segmented image before relaxation.
Figure 37:
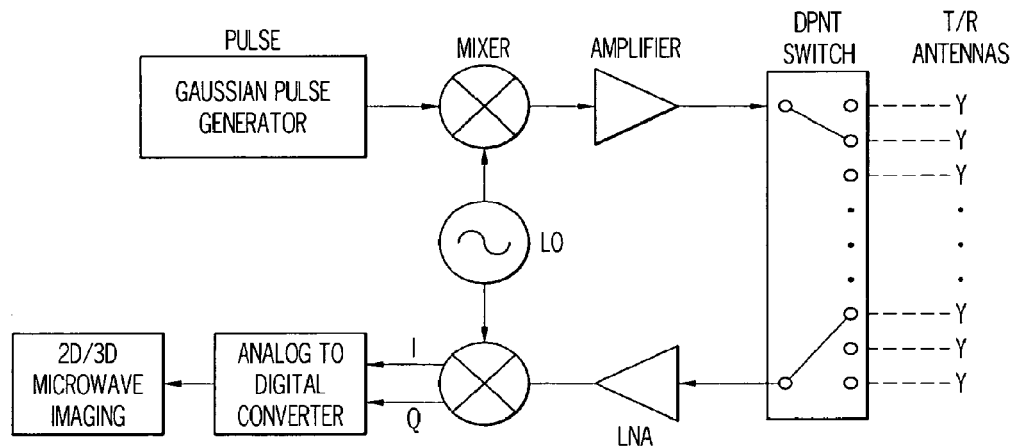
FIG. 37 is an exemplary diagram of a UWB imaging system.
Figure 38:
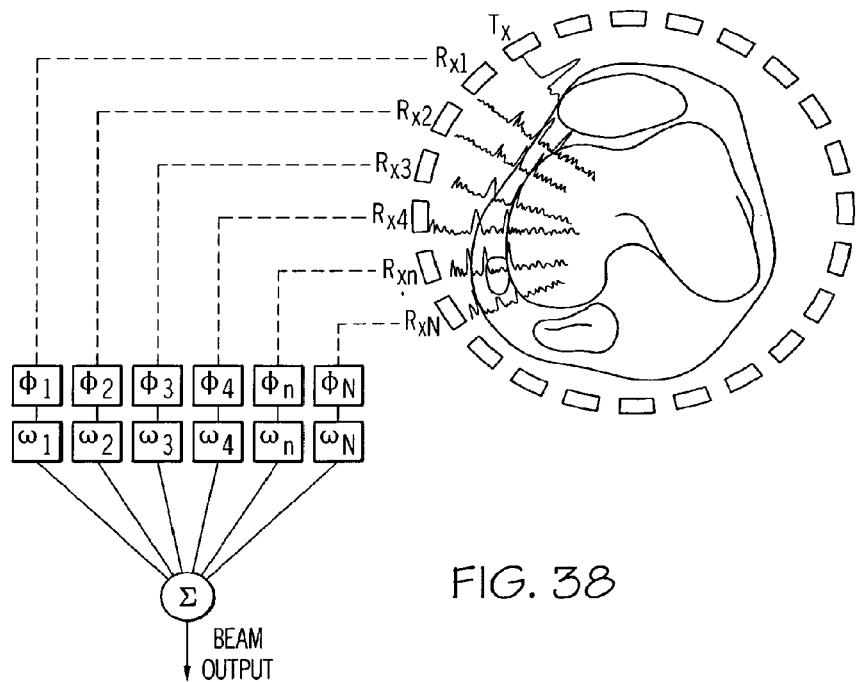
FIG. 38 is an exemplary diagram showing how one signal acts as the transmitter while signals reflected from the knee are received by all of the other UWB antennas.
Figure 39:
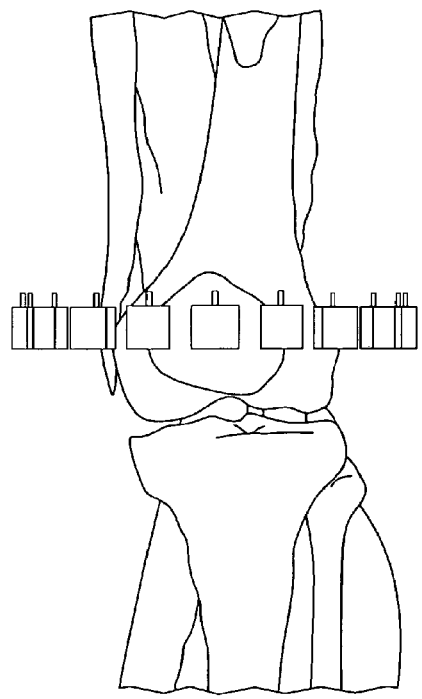
FIG. 39 is an image showing an experimental setup where the UWB antenna array surrounds the circumference of the knee.

Microwave imaging system is comprised of an array where each element acts as both a transmitter and receiver. The system architecture is shown in FIG. 37 where a low noise system clock (clock crystal) triggers a baseband UWB pulse generator (for instance a step recovery diode (SRD) pulse generator). The baseband pulse is upconverted by a local oscillator (LO) via a double balanced wideband mixer. The upconverted signal is amplified and filtered. Finally, the signal is transmitted via a directional microwave antenna. The signal is received at all of the other antennas in the array and is filtered, amplified, downconverted, and low-pass filtered. Next, a sub-sampling mixer triggered by the same low noise system clock is used to time extend the pulse by 1000-100,000×. This effectively reduces the bandwidth of the UWB pulse and allows sampling by a conventional analog-to-digital converter (ADC). Finally, custom digital signal processing algorithms are used for beamforming and creating the final cross sectional image, as shown in FIG. 38. A near-field delay and sum beamformer is used to recover the image. The target scattered signals received by different Rx antennas are equalized in magnitude to compensate for different scattering ratios, propagation losses, and attenuations. Different phase delays of the Rx signals are used for beam steering. The interfaces between various tissue types is detected (air-skin, fat-muscle, cartilage-bone, etc.), as shown in FIG. 15. The experimental setup showing the UWB antenna array, the bones of the knee, and muscles surrounding the knee is shown in FIG. 39.

Figure 40:
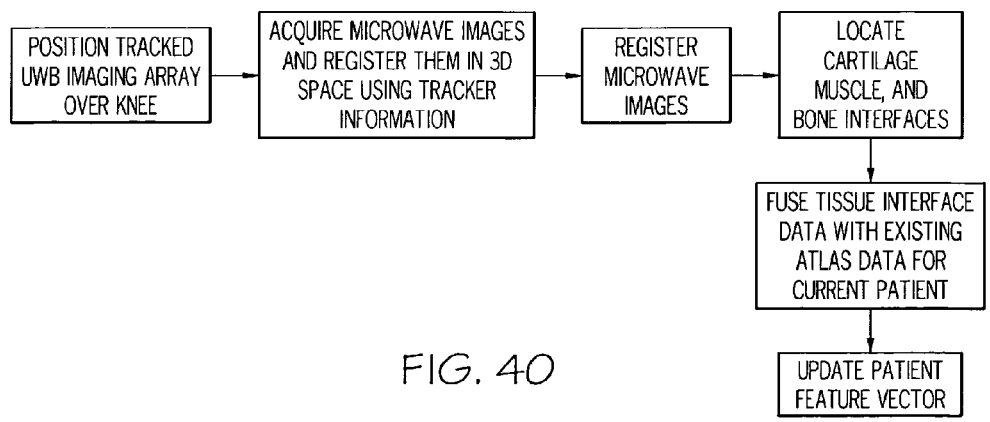
FIG. 40 is a diagram for a microwave imaging process for detection of tissue interfaces at the femur and tibia.

The resultant received signals are used to detect tissue interfaces (i.e. cartilage-bone, fat-muscle, air-skin) from various angles and can also be turned into 2-D cross sectional images. The tissue interface data is added to existing bone and cartilage atlas information for the patient. This results in an extended feature vector to include the UWB imaging data. This process is outlined in FIG. 40. The tracked UWB antenna array is moved along the knee and multiple cross sectional images are obtained. The cross sectional images are registered together and allow a full 3-D analysis of the various tissue interfaces (with emphasis given to the cartilage-bone interface). Information related to these tissue interfaces is added to the feature vector for the patient. This results in additional tissue interface information (i.e. cartilage-bone, soft tissue-cartilage) to be used in bone and cartilage atlas creation and various automated measurements pertaining to the articular cartilage and bones of the knee. Finally, this information can be included in the Bayesian estimation processes for the bone and cartilage atlases.

Figure 41:
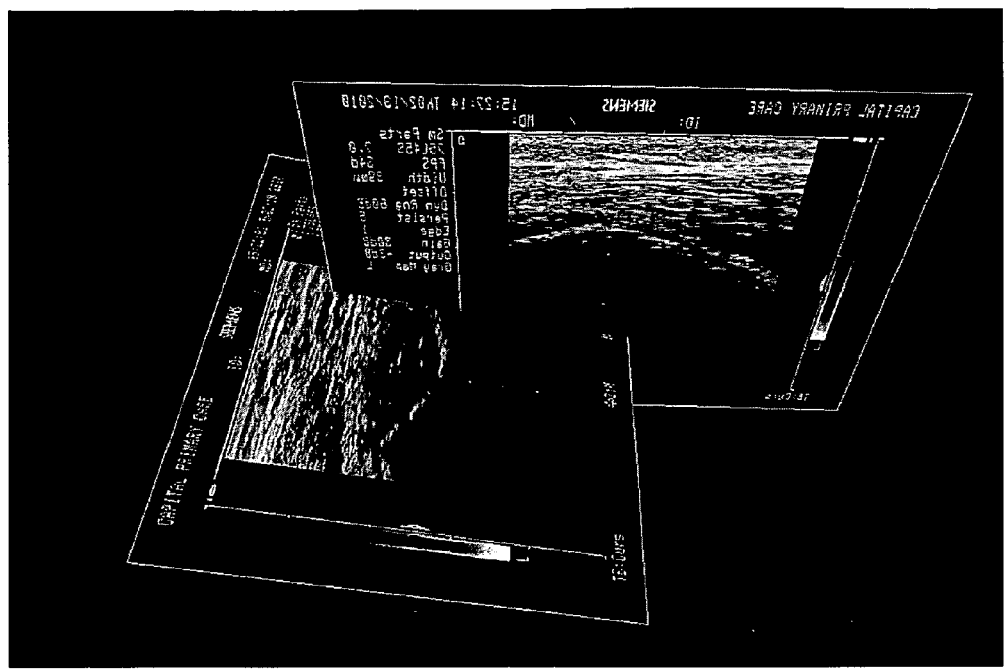
FIG. 41 are exemplary samples of registered ultrasound images acquired from an anterior distal femur.

The system extends a diagnostic B-mode ultrasound machine to add to it the capability of creating patient specific 3D models of the joint bones and cartilage (For example the knee). A localization probe (optical or electromagnetic) is rigidly attached to the ultrasound probe to track its motion while the operator is scanning the joint (for example the knee). The transformation between the motion tracking probe's coordinate frame and the ultrasound probe coordinate frame is determined by a calibration process. The motion tracking probe provides the position (translation) and orientation of each acquired B-mode image (frame) so the acquired images are registered in the 3D Cartesian space as shown in FIG. 41. The set of acquired ultrasound images along with their acquired positions and orientations are then used to reconstruct a volume of the scanned anatomy (similar to the volume reconstructed from CT or MRI)

Figure 42:
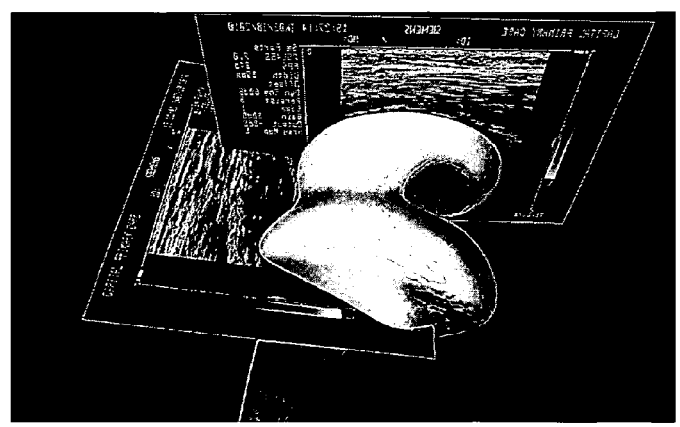
FIG. 42 is an exemplary image of a bone model fit to acquired ultrasound images of the distal femur.

Three or more alignment landmarks (predefined landmarks, like most protruding points on the femoral epicondyles) are then acquired using a tracked A-mode probe or the B-mode probe, and then the mean model of the bone's (the bone to be modeled, for example the femur) atlas is registered with the reconstructed volume using the acquired alignment landmarks using paired points registration. Then the proposed automatic segmentation used for CT and MRI is applied to the reconstructed ultrasound volume, so result in a segmented bone model as shown in FIG. 42.

Figure 43:
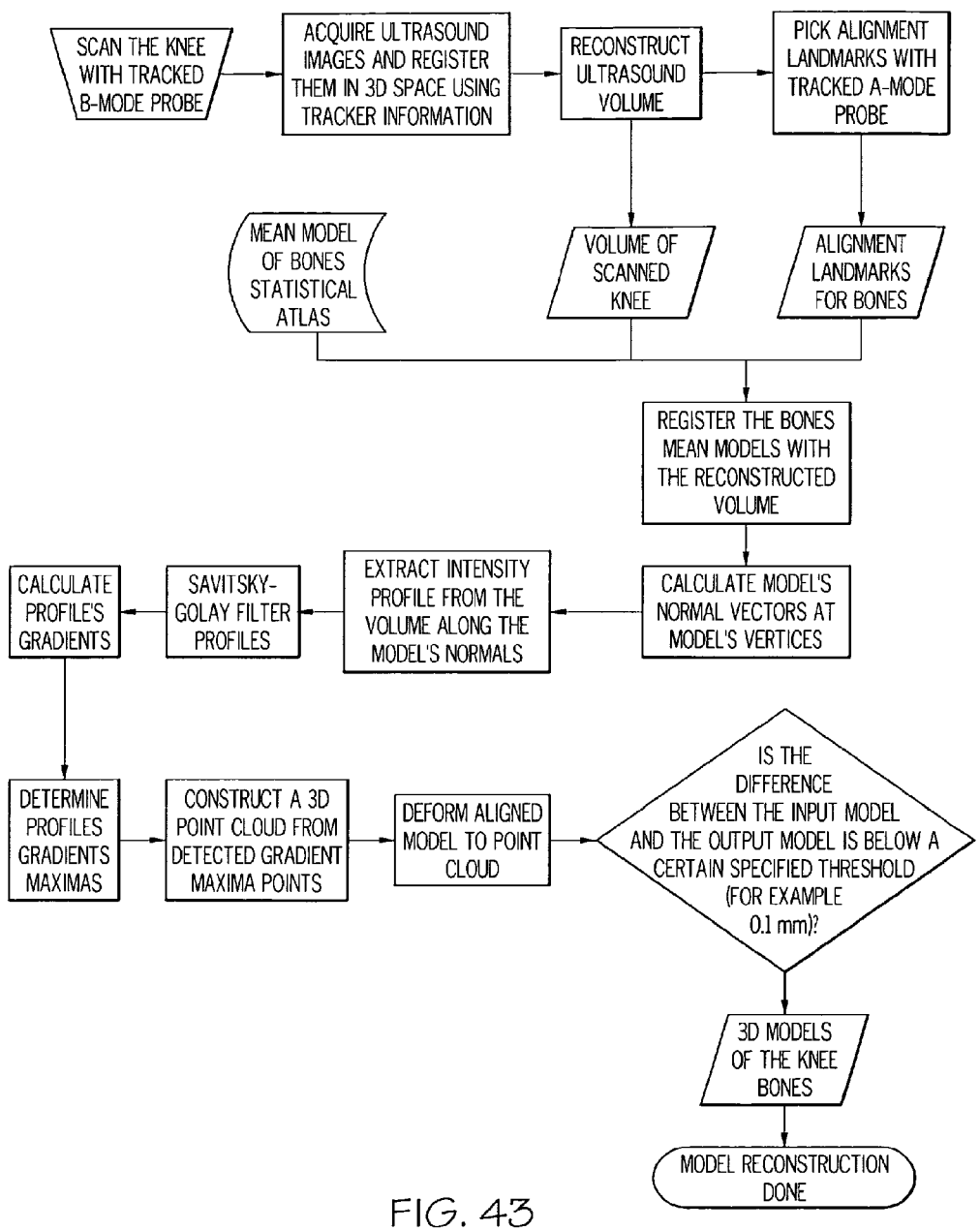
FIG. 43 is a diagram depicting the steps taken to segment using ultrasound.

Flow chart explaining the ultrasound reconstruction system is shown in FIG. 43.

Figure 44:
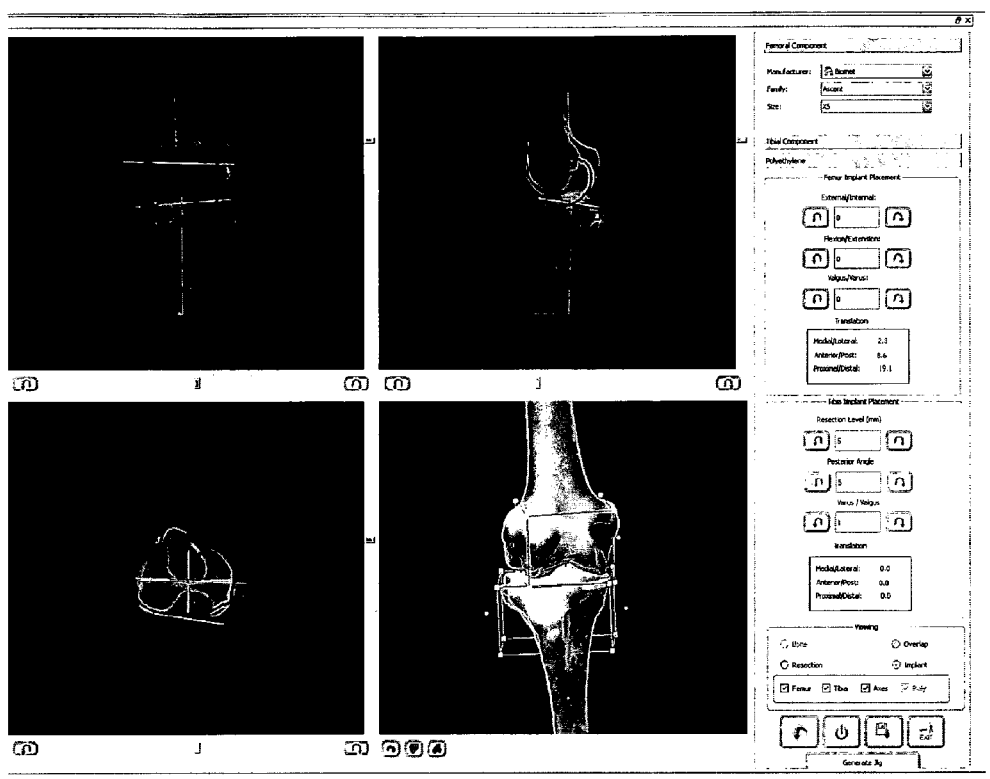
FIG. 44 is a screen shot of a virtual templating subcomponent.

Virtual templating provides the ability to perform implant sizing, placement, and visualization on selected patient bones. Landmarks are automatically calculated with high accuracy and repeatability. Implant sizing is performed along with implant placement. Users then may select particular implants and implant families on which to perform these functions. Users may select from predefined or user-defined surgical techniques for placing the implant components and users may define new surgical techniques for placement of both femoral and tibial components. For example, based on landmarks and axes, users may visualize resections, full intact bones, and/or implants placed on resected bones. For example, in an exemplary embodiment, users may be provided with three 2D orthogonal views and one 3D view for visualization and implant manipulation. Users may modify implant size, family, and manufacturer information. Visualizations may include axes and landmarks overlaid on bones. Fitting results may be saved to the smart database. A surgeon may utilize the various capabilities described herein to perform virtual templating, implant placement, virtual resection, and implant manipulation, thereby producing quantitative results in preoperative templating for the patient and implant alignment. This surgeon edition of the virtual resection runs through the interne utilizing 3D technology in applets (Java3d). Surgeon can modify, accept or deny the templating results. A range of motion is performed to verify implant alignment and placement. The transformation of the placed implant is then used to transform the cutting tools in same alignment as patient. These screw holes are then translated to the jig to translate this placement into the operating room. [FIG. 44]

Figure 45:
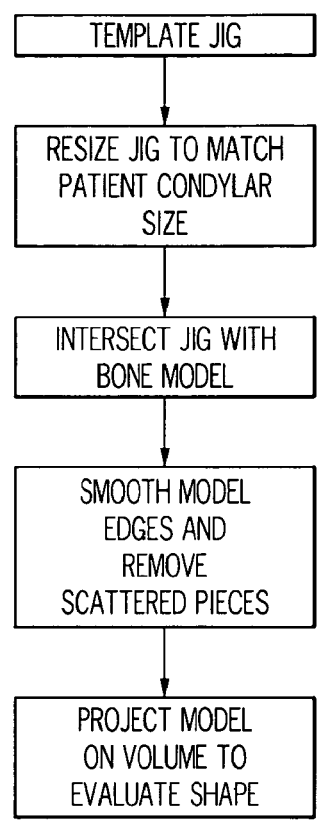
FIG. 45 is an exemplary diagram of a jig creation process.
Figure 46:
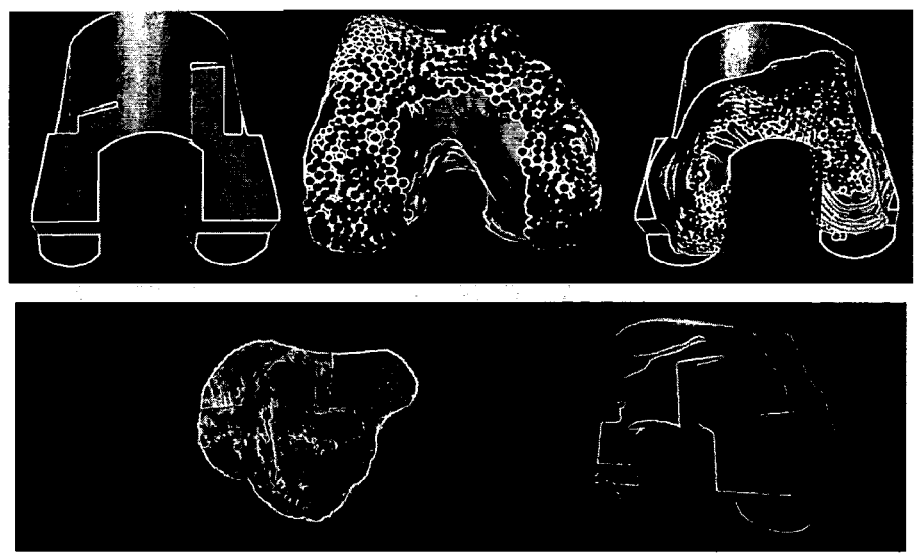
FIG. 46 are sequential images representing certain steps of creating a jig.
Figure 47B:
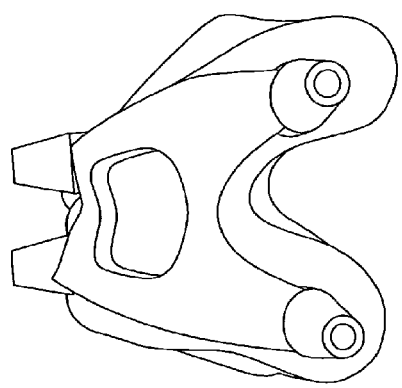
FIG. 47A, FIG. 47B, FIG. 47C, and FIG. 47D are a series of images representing different jig designs with different fixation (a medial and lateral condyle fixation, b curvature fixation, C groove fixation).
Figure 47D:
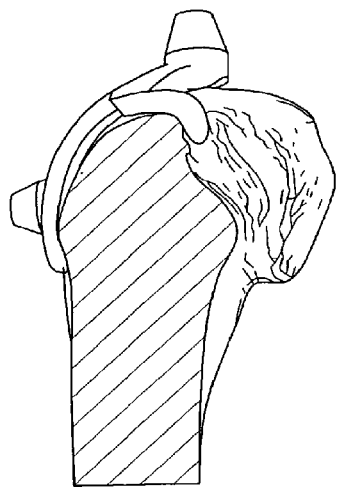
Figure 47A:
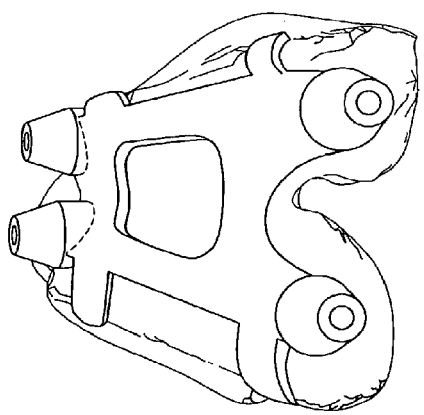
Figure 47C:
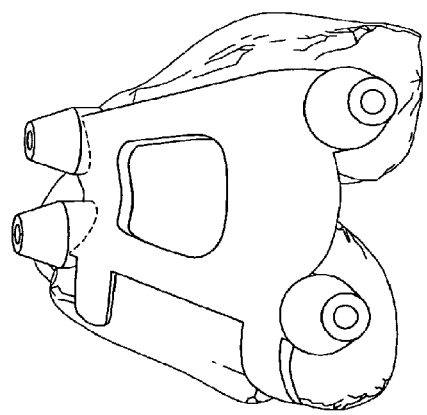
Figure 48A:
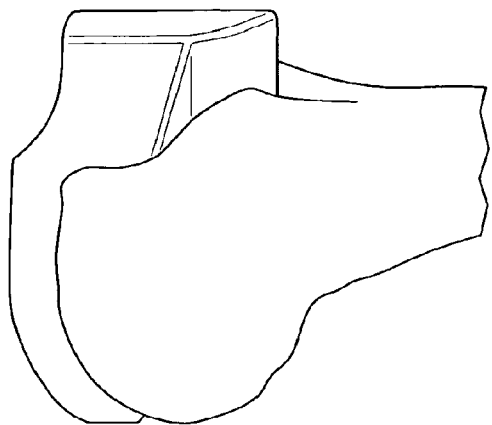
FIG. 48A, FIG. 48B, FIGS. 48C, and 48D are a series of images showing a femoral and tibial cutting jig for use in a knee revision surgical procedure.
Figure 48B:
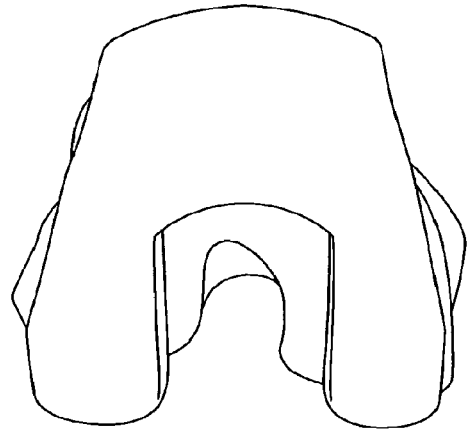
Figure 48C:
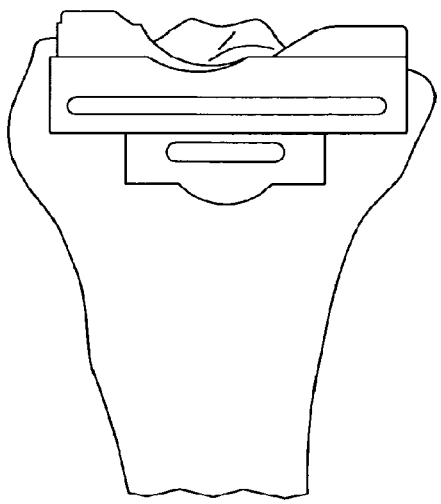
Figure 48D:
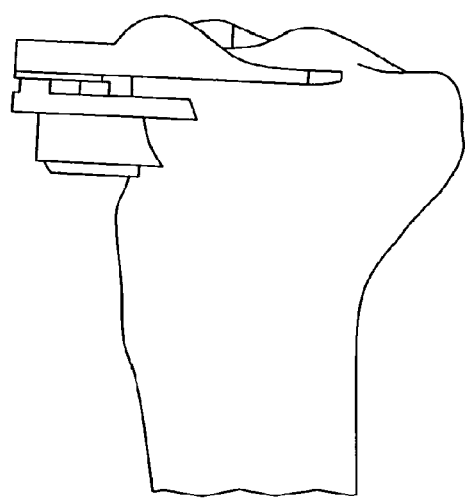

FIGS. 45,46 outline the process of jig creation, this process utilizes a template jig that is placed on the average bone from our statistical atlas. this jig is then resized to match the size of the patient femoral condyles and tibial plateau. Both tibia and femur models are then intersected with the patient specific 3D bone models to create a unique patient imprint on the inside of the jig that guarantees tight fit during surgery.

FIG. 47 highlights different jig design philosophies for different level of joint degeneracy. FIG. 48 shows output femoral and tibial jig from the system.

Figure 49:
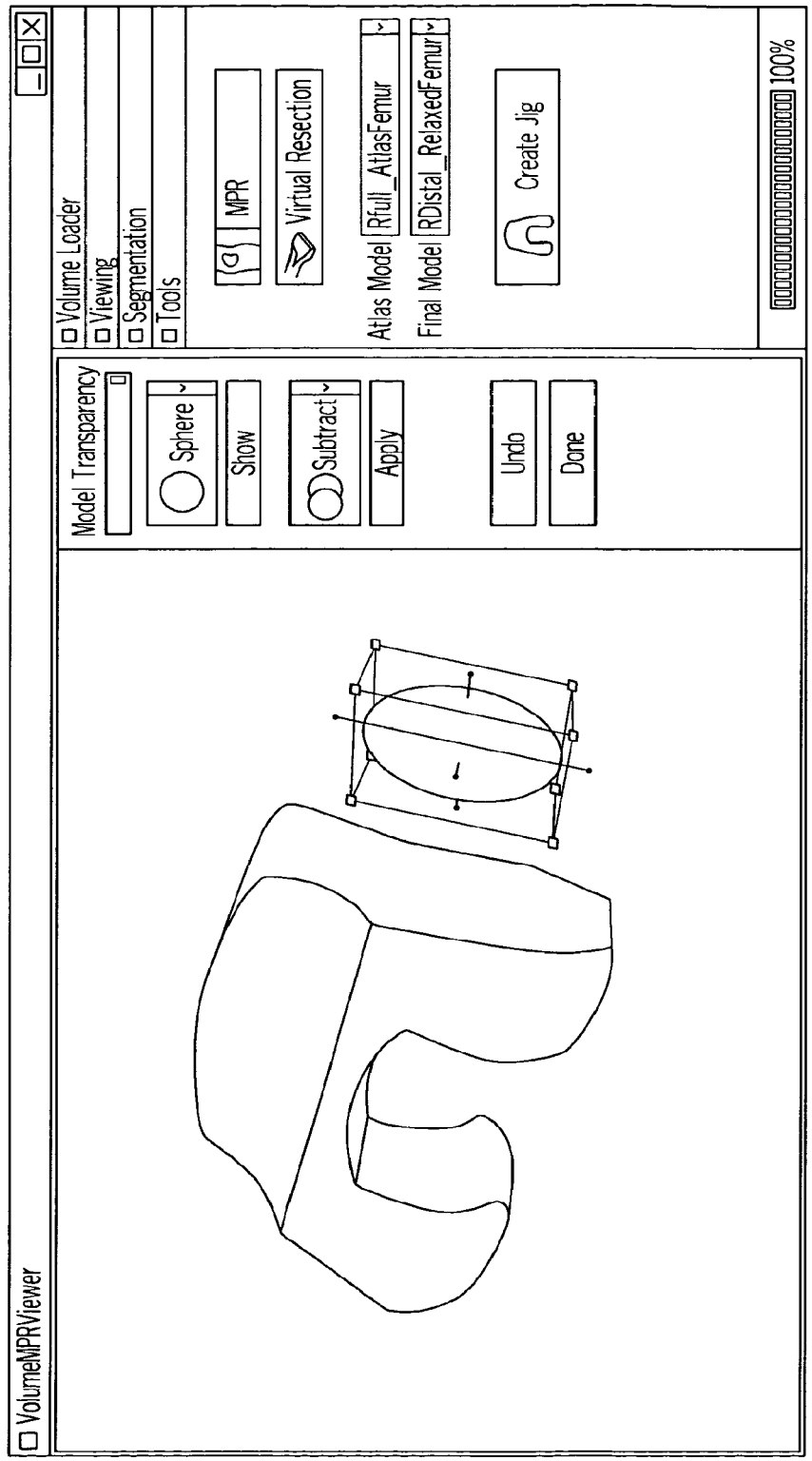
FIG. 49 is a screen shot of a CAD editor for modifying the 3D output jig model.

FIG. 49 shows editor for polishing and verifying the automatically created jig.

Figure 50:
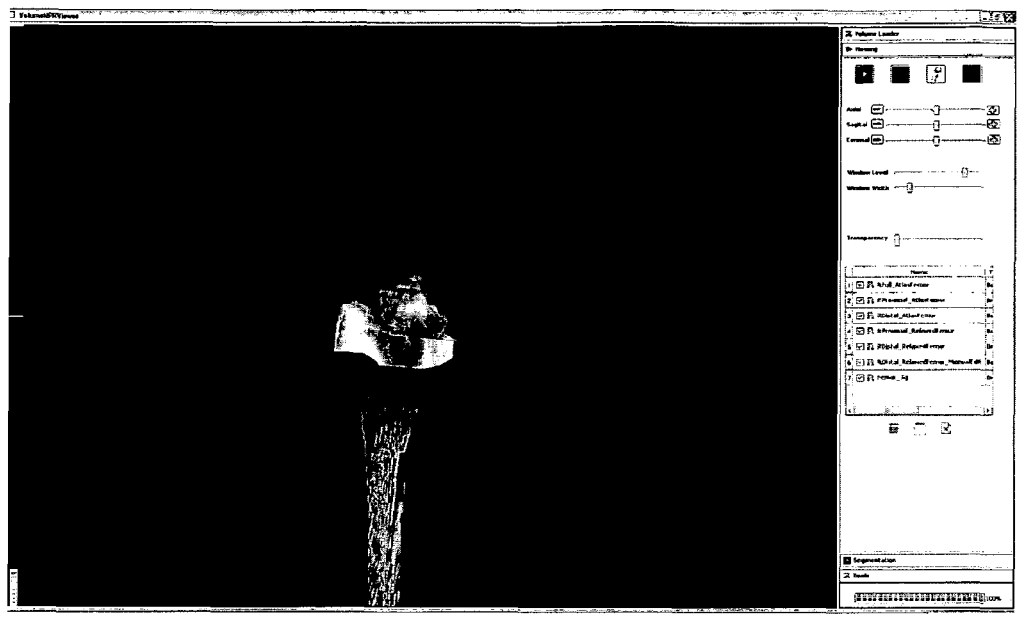
FIG. 50 is a screen shot of an evaluation of a jig with respect to original CT data.

FIG. 50 shows process of verifying the output jig by projecting it on the same space as the patient volumetric data.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A reconstruction system for generating a patient-specific bone shell representative of at least a portion of a patient's bone in its current state comprising:
    a recognition module configured for receiving a plurality of 2D images of a portion of a patient's anatomy, the recognition module recognizing from the plurality of 2D image slices at least a bone segment comprising an enclosed boundary corresponding to an exterior of the patient's bone;
    a construction module to produce and output a 3D image bone shell of at least the portion of the patient's bone by associating the plurality of 2D images of the patient's bone based on the recognition of the enclosed boundary of each bone segment, where the 3D image bone shell depicts a current state of the patient's bone.

2. The reconstruction system of claim 1, wherein the plurality of 2D images are computed tomography images.

3. The reconstruction system of claim 1, wherein the 3D image bone shell is representative of at least one of a femur, a tibia, and a humerus.

4. The reconstruction system of claim 1, further comprising a generation module to generate a 3D image surgical jig to mate with said 3D image bone shell, where the 3D image surgical jig includes topographical features customized to the exterior features of the 3D image bone shell.

5. The reconstruction system of claim 4, wherein the generation module outputs an instruction file for fabricating a surgical jig having tangible topographical features of the 3D image surgical jig.

6. The reconstruction system of claim 1, wherein the recognition module recognizes an outline of cartilage appearing in at least one said 2D images, and further wherein the construction module produces a 3D image cartilage shell representing at least a portion of a patient's cartilage using the plurality of 2D images of the patient's anatomy based on the recognition of the outline of cartilage.

7. The reconstruction system of claim 6, wherein the recognition module recognizes the outline of cartilage appearing in at least one said 2D images by determining cartilage thickness using at least one of statistical shape atlases and Bayesian inversion probabilities.

8. The reconstruction system of claim 1, wherein the recognition module enables interactive intervention for at least one of contour adding, subtracting and painting.

9. The reconstruction system of claim 1, wherein each of the plurality of 2D images is orthogonal to an axis extending through the patient's anatomy.

10. The reconstruction system according to claim 1, wherein the recognition module recognizes the enclosed boundary of each bone segment on the 2D images by using a template 3D image bone shell that is not patient specific.

11. The reconstruction system of claim 10, wherein the template 3D image bone shell that is not patient specific is obtained from a library of bone models.

* * * * *